(12) United States Patent
Gross et al.

(10) Patent No.: US 7,636,597 B2
(45) Date of Patent: Dec. 22, 2009

(54) SURGICAL TOOLS AND TECHNIQUES FOR STIMULATION

(75) Inventors: Yossi Gross, Moshav Mazor (IL); Alon Shalev, Ra'anana (IL); Raphael Benary, Tel Aviv (IL); Adi Lorian, Tiberias (IL)

(73) Assignee: Brainsgate, Ltd., Caesarea (IL)

( * ) Notice: Subject to any disclaimer, the term of this patent is extended or adjusted under 35 U.S.C. 154(b) by 379 days.

(21) Appl. No.: 10/535,024

(22) PCT Filed: Nov. 13, 2003

(86) PCT No.: PCT/IL03/00966

§ 371 (c)(1),
(2), (4) Date: Dec. 27, 2005

(87) PCT Pub. No.: WO2004/043218

PCT Pub. Date: May 27, 2004

(65) Prior Publication Data

US 2006/0195169 A1 Aug. 31, 2006

Related U.S. Application Data

(60) Provisional application No. 60/426,180, filed on Nov. 14, 2002.

(51) Int. Cl.
*A61N 1/00* (2006.01)
(52) U.S. Cl. .......................................................... 607/2
(58) Field of Classification Search .................. 607/1, 607/2, 45, 46
See application file for complete search history.

(56) References Cited

U.S. PATENT DOCUMENTS 4,666,829 A 5/1987 Glenner et al.
(Continued)

FOREIGN PATENT DOCUMENTS

EP 1559369 8/2005
(Continued)

OTHER PUBLICATIONS

Suzuki, N. et al., "Effect on Cortical Blood Flow of Electrical Stimulation of Trigeminal Cerebrovascular Nerve Fibers in the Rat", Acta Physiol. Scand., 138, 307-315, 1990.
(Continued)

*Primary Examiner*—Scott M Getzow
(74) *Attorney, Agent, or Firm*—RatnerPrestia

(57) ABSTRACT

Apparatus for treating a subject is provided, the apparatus comprising (a) a stimulation device (352), adapted to be implanted in a vicinity of a site selected from the list consisting of: a sphenopalatine ganglion (SPG) (52) of the subject and a neural tract originating in or leading to the SPG; and (b) a connecting element (356), coupled to the stimulation device (352), and adapted to be passed through at least a portion of a greater palatine canal (282) of the subject. Also provided is a method for implanting a treatment stimulation device (352) in a vicinity of a site of a subject, the method comprising passing the device (352) through a greater palatine foramen (22) of the subject, and bringing the device (352) into contact with the vicinity of the site, the site selected from the list consisting of: a sphenopalatine ganglion (SPG) (52) of the subject and a neural tract originating in or leading to the SPG.

67 Claims, 13 Drawing Sheets

U.S. PATENT DOCUMENTS

| | | |
|---|---|---|
| 4,866,042 A | 9/1989 | Neuwelt |
| 4,874,694 A | 10/1989 | Gandy et al. |
| 4,979,511 A | 12/1990 | Terry, Jr. |
| 5,011,472 A | 4/1991 | Aebischer et al. |
| 5,031,618 A | 7/1991 | Mullett |
| 5,059,415 A | 10/1991 | Neuwelt |
| 5,154,172 A | 10/1992 | Terry, Jr. et al. |
| 5,179,950 A | 1/1993 | Stanislaw |
| 5,186,170 A | 2/1993 | Varrichio et al. |
| 5,188,104 A | 2/1993 | Wernicke |
| 5,205,285 A | 4/1993 | Baker, Jr. |
| 5,215,086 A | 6/1993 | Terry, Jr. |
| 5,215,089 A | 6/1993 | Baker, Jr. |
| 5,222,494 A | 6/1993 | Baker, Jr. |
| 5,223,254 A | 6/1993 | Paradiso et al. |
| 5,231,988 A | 8/1993 | Wernicke et al. |
| 5,235,980 A | 8/1993 | Varrichio et al. |
| 5,237,991 A | 8/1993 | Baker, Jr. et al. |
| 5,251,634 A | 10/1993 | Weinberg |
| 5,263,480 A | 11/1993 | Wernicke |
| 5,268,164 A | 12/1993 | Kozarich et al. |
| 5,269,303 A | 12/1993 | Wernicke et al. |
| 5,299,569 A | 4/1994 | Wernicke |
| 5,304,206 A | 4/1994 | Baker, Jr. et al. |
| 5,304,632 A | 4/1994 | Vaudry et al. |
| 5,330,515 A | 7/1994 | Rutecki et al. |
| 5,335,657 A | 8/1994 | Terry, Jr. |
| 5,351,394 A | 10/1994 | Weinberg |
| 5,514,131 A | 5/1996 | Edwards et al. |
| 5,531,778 A | 7/1996 | Maschino et al. |
| 5,540,730 A | 7/1996 | Terry, Jr. |
| 5,571,150 A | 11/1996 | Wernicke |
| 5,639,853 A | 6/1997 | Paradiso et al. |
| 5,707,400 A | 1/1998 | Terry, Jr. |
| 5,752,515 A | 5/1998 | Jolesz et al. |
| 5,756,071 A | 5/1998 | Mattern et al. |
| 5,792,100 A | 8/1998 | Shantha |
| 5,830,670 A | 11/1998 | De la Monte et al. |
| 5,833,988 A | 11/1998 | Friden |
| 5,849,600 A | 12/1998 | Nixon et al. |
| 5,928,272 A | 7/1999 | Adkins et al. |
| 5,938,689 A | 8/1999 | Fischell et al. |
| 5,938,690 A | 8/1999 | Law et al. |
| 5,981,194 A | 11/1999 | Jefferies et al. |
| 5,985,581 A | 11/1999 | Nixon et al. |
| 6,001,331 A | 12/1999 | Caprathe et al. |
| 6,005,004 A | 12/1999 | Katz et al. |
| 6,006,124 A | 12/1999 | Fischell et al. |
| 6,016,449 A | 1/2000 | Fischell et al. |
| 6,061,593 A | 5/2000 | Fischell et al. |
| 6,066,163 A | 5/2000 | John |
| 6,071,705 A | 6/2000 | Wands et al. |
| 6,087,118 A | 7/2000 | Aronson et al. |
| 6,114,175 A | 9/2000 | Klunk et al. |
| 6,117,454 A | 9/2000 | Kreuter et al. |
| 6,128,538 A | 10/2000 | Fischell et al. |
| 6,130,048 A | 10/2000 | Nixon |
| 6,132,977 A | 10/2000 | Thompson et al. |
| 6,134,474 A | 10/2000 | Fischell et al. |
| 6,161,045 A | 12/2000 | Fischell et al. |
| 6,200,768 B1 | 3/2001 | Mandelkow et al. |
| 6,210,895 B1 | 4/2001 | Schipper et al. |
| 6,211,235 B1 | 4/2001 | Wu et al. |
| 6,230,049 B1 | 5/2001 | Fischell et al. |
| 6,232,326 B1 | 5/2001 | Nelson |
| 6,238,892 B1 | 5/2001 | Mercken et al. |
| 6,277,841 B1 | 8/2001 | Rajagopalan et al. |
| 6,287,793 B1 | 9/2001 | Schenk et al. |
| 6,322,494 B1 | 11/2001 | Bullivant et al. |
| 6,325,475 B1 | 12/2001 | Hayes et al. |
| 6,329,531 B1 | 12/2001 | Turner et al. |
| 6,338,715 B1 | 1/2002 | Hayes et al. |
| 6,353,754 B1 | 3/2002 | Fischell et al. |
| 6,354,299 B1 | 3/2002 | Fischell et al. |
| 6,358,681 B2 | 3/2002 | Ginsberg et al. |
| 6,360,122 B1 | 3/2002 | Fischell et al. |
| 6,405,079 B1 | 6/2002 | Ansarinia |
| 6,410,046 B1 | 6/2002 | Lerner |
| 6,427,086 B1 | 7/2002 | Fischell et al. |
| 6,432,986 B2 | 8/2002 | Levin |
| 6,459,936 B2 | 10/2002 | Fischell et al. |
| 6,466,822 B1 | 10/2002 | Pless |
| 6,473,639 B1 | 10/2002 | Fischell et al. |
| 6,473,644 B1 | 10/2002 | Terry, Jr. et al. |
| 6,480,743 B1 | 11/2002 | Kirkpatrick et al. |
| 6,491,940 B1 | 12/2002 | Levin |
| 6,526,318 B1 | 2/2003 | Ansarinia |
| 6,529,774 B1 | 3/2003 | Greene |
| 6,531,454 B1 | 3/2003 | Leary et al. |
| 6,587,719 B1 | 7/2003 | Barrett et al. |
| 6,587,724 B2 | 7/2003 | Mann |
| 6,591,137 B1 | 7/2003 | Fischell et al. |
| 6,591,138 B1 | 7/2003 | Fischell et al. |
| 6,597,953 B2 | 7/2003 | Boling |
| 6,597,954 B1 | 7/2003 | Pless et al. |
| 6,606,521 B2 | 8/2003 | Paspa et al. |
| 6,609,025 B2 | 8/2003 | Barrett et al. |
| 6,609,032 B1 | 8/2003 | Woods et al. |
| 6,609,956 B2 | 8/2003 | Margaria |
| 6,618,623 B1 | 9/2003 | Pless et al. |
| 6,622,038 B2 | 9/2003 | Barrett et al. |
| 6,622,041 B2 | 9/2003 | Terry, Jr. et al. |
| 6,622,047 B2 | 9/2003 | Barrett et al. |
| 6,647,296 B2 | 11/2003 | Fischell et al. |
| 6,662,035 B2 | 12/2003 | Sochor |
| 6,678,553 B2 | 1/2004 | Lerner et al. |
| 6,690,974 B2 | 2/2004 | Archer et al. |
| 6,735,474 B1 | 5/2004 | Loeb et al. |
| 6,810,285 B2 | 10/2004 | Pless et al. |
| 6,811,788 B2 | 11/2004 | Yu |
| 6,853,858 B2 | 2/2005 | Shalev |
| 6,905,827 B2 | 6/2005 | Wohlgemuth et al. |
| 2001/0004644 A1 | 6/2001 | Levin |
| 2001/0014670 A1 | 8/2001 | Balin et al. |
| 2001/0018191 A1 | 8/2001 | Mercken et al. |
| 2001/0020097 A1 | 9/2001 | Audia et al. |
| 2001/0026916 A1 | 10/2001 | Ginsberg et al. |
| 2001/0027309 A1 | 10/2001 | Elsberry |
| 2001/0044126 A1 | 11/2001 | Holtzman et al. |
| 2001/0047014 A1 | 11/2001 | Alanine et al. |
| 2001/0051633 A1 | 12/2001 | Bigge et al. |
| 2002/0002270 A1 | 1/2002 | Zinkowski et al. |
| 2002/0006627 A1 | 1/2002 | Reitz et al. |
| 2002/0009445 A1 | 1/2002 | Du et al. |
| 2002/0019016 A1 | 2/2002 | Vanmechelen et al. |
| 2002/0019412 A1 | 2/2002 | Andersen et al. |
| 2002/0019519 A1 | 2/2002 | Bingham et al. |
| 2002/0022242 A1 | 2/2002 | Small et al. |
| 2002/0022593 A1 | 2/2002 | Yue |
| 2002/0022621 A1 | 2/2002 | Chaturvedula et al. |
| 2002/0022650 A1 | 2/2002 | Posmantur et al. |
| 2002/0025955 A1 | 2/2002 | Han et al. |
| 2002/0026652 A1 | 2/2002 | Allen et al. |
| 2002/0028462 A1 | 3/2002 | Tanzi et al. |
| 2002/0028834 A1 | 3/2002 | Villalobos et al. |
| 2002/0035145 A1 | 3/2002 | Tsai et al. |
| 2002/0040032 A1 | 4/2002 | Glasky et al. |
| 2002/0040052 A1 | 4/2002 | Ito et al. |
| 2002/0042121 A1 | 4/2002 | Riesner et al. |
| 2002/0042420 A1 | 4/2002 | Briem et al. |
| 2002/0044919 A1 | 4/2002 | Yu |
| 2002/0052311 A1 | 5/2002 | Solomon et al. |
| 2002/0055501 A1 | 5/2002 | Olson et al. |
| 2002/0066959 A1 | 6/2002 | Joshi |

| | | |
|---|---|---|
| 2002/0068080 A1 | 6/2002 | Lerner |
| 2002/0082583 A1 | 6/2002 | Lerner |
| 2002/0099412 A1 | 7/2002 | Fischell et al. |
| 2002/0099417 A1 | 7/2002 | Naritoku et al. |
| 2002/0123678 A1 | 9/2002 | Lerner et al. |
| 2002/0133841 A1 | 9/2002 | Leviten |
| 2002/0169307 A1 | 11/2002 | Klein |
| 2002/0169485 A1 | 11/2002 | Pless et al. |
| 2002/0183683 A1 | 12/2002 | Lerner |
| 2003/0005473 A1 | 1/2003 | Brennan et al. |
| 2003/0005477 A1 | 1/2003 | Leviten |
| 2003/0013136 A1 | 1/2003 | Balser et al. |
| 2003/0014772 A1 | 1/2003 | Allen |
| 2003/0018989 A1 | 1/2003 | Brennan et al. |
| 2003/0036781 A1 | 2/2003 | Nuttin et al. |
| 2003/0051268 A1 | 3/2003 | Allen |
| 2003/0056238 A1 | 3/2003 | Wisotzkey |
| 2003/0073917 A1 | 4/2003 | Echauz et al. |
| 2003/0074033 A1 | 4/2003 | Pless et al. |
| 2003/0106083 A1 | 6/2003 | Allen |
| 2003/0131367 A1 | 7/2003 | Guenther et al. |
| 2003/0133877 A1 | 7/2003 | Levin |
| 2003/0144711 A1 | 7/2003 | Pless et al. |
| 2003/0149457 A1 | 8/2003 | Tcheng et al. |
| 2003/0166099 A1 | 9/2003 | Sabbadini et al. |
| 2003/0166279 A1 | 9/2003 | Sabbadini et al. |
| 2003/0172390 A1 | 9/2003 | Wisotzkey et al. |
| 2003/0176892 A1 | 9/2003 | Shalev |
| 2003/0176898 A1 | 9/2003 | Gross et al. |
| 2003/0177514 A1 | 9/2003 | Leviten |
| 2003/0190601 A1 | 10/2003 | Sabbadini et al. |
| 2003/0190683 A1 | 10/2003 | Sabbadini et al. |
| 2003/0190749 A1 | 10/2003 | Surber et al. |
| 2003/0191426 A1 | 10/2003 | Lerner et al. |
| 2003/0194714 A1 | 10/2003 | Sabbadini et al. |
| 2003/0195588 A1 | 10/2003 | Fischell et al. |
| 2003/0195602 A1 | 10/2003 | Boling |
| 2003/0198995 A1 | 10/2003 | Sabbadini |
| 2003/0198996 A1 | 10/2003 | Surber et al. |
| 2003/0199005 A1 | 10/2003 | Sabbadini et al. |
| 2003/0199088 A1 | 10/2003 | Sabbadini et al. |
| 2003/0199089 A1 | 10/2003 | Surber et al. |
| 2003/0202937 A1 | 10/2003 | Sabbadini et al. |
| 2003/0203411 A1 | 10/2003 | Sabbadini et al. |
| 2003/0203481 A1 | 10/2003 | Surber et al. |
| 2003/0207833 A1 | 11/2003 | Berkley et al. |
| 2003/0211086 A1 | 11/2003 | Berkley et al. |
| 2003/0211599 A1 | 11/2003 | Sabbadini et al. |
| 2003/0219408 A1 | 11/2003 | Sabbadini et al. |
| 2003/0219888 A1 | 11/2003 | Segall et al. |
| 2003/0224369 A1 | 12/2003 | Surber et al. |
| 2003/0224444 A1 | 12/2003 | Sabbadini et al. |
| 2003/0232335 A1 | 12/2003 | Surber et al. |
| 2004/0015068 A1 | 1/2004 | Shalev et al. |
| 2004/0033491 A1 | 2/2004 | Alsobrook et al. |
| 2004/0054297 A1 | 3/2004 | Wingeier et al. |
| 2004/0133248 A1 | 7/2004 | Frei et al. |
| 2004/0136950 A1 | 7/2004 | Ni et al. |
| 2004/0136951 A1 | 7/2004 | Ni et al. |
| 2004/0153129 A1 | 8/2004 | Pless et al. |
| 2004/0210269 A1 | 10/2004 | Shalev et al. |
| 2004/0220644 A1 | 11/2004 | Shalev et al. |
| 2005/0020519 A1 | 1/2005 | Albiston et al. |
| 2005/0054939 A1 | 3/2005 | Ben-Ari et al. |
| 2005/0074506 A1 | 4/2005 | Natan et al. |
| 2005/0112090 A9 | 5/2005 | Ni et al. |
| 2005/0118187 A1 | 6/2005 | Yu |
| 2005/0137646 A1 | 6/2005 | Wallace et al. |
| 2005/0137647 A1 | 6/2005 | Wallace et al. |
| 2005/0159790 A1 | 7/2005 | Shalev |

FOREIGN PATENT DOCUMENTS

| | | |
|---|---|---|
| WO | WO-97/18855 | 5/1997 |
| WO | WO-99/03473 | 1/1999 |
| WO | WO-00/44432 | 8/2000 |
| WO | WO-00/73343 | 12/2000 |
| WO | WO-01/00402 A1 | 1/2001 |
| WO | WO-01/43733 | 6/2001 |
| WO | WO-01/85094 A2 | 11/2001 |
| WO | WO-01/97905 A1 | 12/2001 |
| WO | WO-02/09419-AK | 11/2002 |
| WO | WO-03/063959 | 8/2003 |
| WO | WO-2004/010923 | 2/2004 |
| WO | WO-2004/043217 | 5/2004 |
| WO | WO-2004/043218 | 5/2004 |
| WO | WO-2004/043334 | 5/2004 |
| WO | WO-2004/044947 | 5/2004 |
| WO | WO-2004/045242 | 5/2004 |
| WO | WO-2004/064918 A1 | 8/2004 |

OTHER PUBLICATIONS

Fusco BM, Fiore G, Gallo F, Martelletti P, Giacovazzo M, "Capsaicin-sensitive sensory neurons in cluster headache: pathophysiological aspects and therapeutic indications," Headache, 34, 132-137 (1994).

Lambert GA, Bogduk N, Goadsby PJ, Duckworth JW, Lance JW, "Decreased carotid arterial resistance in cats in response to trigeminal stimulation," Journal of Neurosurgery, 61, 307-315 (1984).

Silver WL, "Neural and pharmacological basis for nasal irritation," in Tucker WG, Leaderer BP, Molhave L, Cain WS (eds), Sources of Indoor Air Contaminants, Ann. NY Acad. Sci., 641, 152-163 (1992).

J.M. Gallo, et al., "The effect of P-glycoprotein on Paclitaxel Brain and Brain Tumor Distribution in Mice" Cancer Research 63, 5114-5117, Aug. 2003.

Branimir I. Sikic, et al., "Modulation and preventiion of multidrug resistance by inhibitors of P-glycoprotein", Cancer Chemother Pharmacol (1997), 40 (Suppl):S13-S19.

Fu Yung-Hui, et al., "Improved bioavailability of orally administered drugs by Chinese herbal enhancers through modulation of P-glycoprotein", ASHP 39th Midyear Clinical Meeting and Exhibits, Dec. 5-9, 2004.

Delephine, et al., "Plasma Protein Extravasation Induced in the Rat Dura Mater by Stimulation of the Parasympathetic Sphenopalatine Ganglion" Experimental Neurology, 147, 389-400, 1997.

Hara H. Zhang, et al., "Parasympathetic Cerebrovascular Innervation: An Anterograde Tracing from the Sphenopalatine Ganglion in the Rat", Neurosurgery, 32 822-827, 1993.

G.L. Ruskell,"The Orbital Branches of the Pterygopalatine Ganglion and their Relationship with Internal Carotide Nerve Branches in Primates" J. Anat. 1970,106,2, pp. 323-339.

Kroll RA, Neuwelt EA, "Outwitting the Blood Brain Barrier for Therapeutic Purposes: Osmotic Opening and Other Means", Neurosurgery, 42,1083-1100, 1998.

Sanders M, et al., "Efficacy of Sphenopalatine Ganglion Blockade in 66 Patients Suffering from Cluster Headache: A 12-70 Month Follow-Up Evaluation", Journal of Neurosurgery, 87 876-880, 1997.

Suzuki, N. et al. "Selective Electrical Stimulation of postganglionic Cerebrovascular Parasympathetic Nerve Fibers Originating from the Sphenopalatine Ganglion Enhances Cortical Blood Flow in the Rat" Journal Of Cerebral Blood Flow and Metabolism, 10 383-391 (1990).

Samad TA et al., in an article entitled, "Interleukin-1beta-mediatyed induction of Cox-2 in the CNS contributes to inflammatory pain hypersensitivity," in Nature 410(6827): 471-5 (2001).

Van de WaterBeemd, et al., "Estimation of Blood Brain Barrier Crossing of Drugs Using Molecular Sze and Shape and H bonding Descriptors" Journal of Drug Targeting, 6, 151-165, 1998.

Ronald F. Young, "Electrical Stimulation of the Trigeminal nerve root for the Treatment of Chronic Facial Pain", J Neurosurg 83:72-78, 1995.

N. Suzuki, et al., "Origins and Pathways of Cerebrovascular Vasoactive Intestinal Polypeptide-Positive Nerves in Rat" J Cereb Blood Flow Metab. vol. 8 No. 5, 1988.

European Search Report, dated Dec. 13, 2006 for Application No. EP 06 01 7239.

Hotta H et al., in an article entitled, "Effects of stimulating the nucleus basalis of Meynert on blood flow and delayed neuronal death following transient ischemia in rat cerebral cortes," Jap J Phys 52:383-393 (2002).

Segher O et al., in an article entitled, "Spinal cord stimulation reducing infract volume in model of focal cerebral ischemia in rats," J NeuroSurg 99(1):131-137 (2003).

Goadsby PJ et al., "Effect of stimulation of trigeminal ganglion on regional cerebral blood flow in cats," Am J Physiol 22:R270-R274 (1987).

Matsui T et al., in an article entitled, "The effects of cervical spinal cord stimulation (cSCS) on experimental stroke," Pacing Clin Electrophysiol 12(4 Pt 2):726-32 (1989).

Suzuki N et al., "Trigeminal fibre collaterals storing substance P and calcitonin gene-related peptide associate with ganglion cells containing choline acetyltransferase and vasoactive intestinal polypeptide in the sphenopalatine ganglion of the rat. An axon reflex modulating parasympathetic ganglionic activity?" Neuroscience 30:595-604 (1989).

Walters BB et al., "Cerebrovascular projections from the sphenopalatine and otic ganglia to the middle cerebral artery of the cat," Stroke 17:488-494 (1986).

Branston NM, "The physiology of the cerebrovascular parasympathetic innervation," British Journal of Neurosurgery 9:319-329 (1995).

Branston NM et al., "Contribution of cerebrovascular parasympathetic and sensory innervation to the short-term control of blood flow in rat cerebral cortex," J Cereb Blood Flow Metab 15(3):525-31 (1995).

Sun Y et al., "Neuronal nitric oxide synthase and ischemia-induced neurogenesis," J Cereb Blood Flow Metab 25(4):485-92 (2005).

Zhang F et al., "Nitric oxide donors increase blood flow and reduce brain damage in focal ischemia: evidence that nitric oxide is beneficial in the early stages of cerebral ischemia," J Cereb Blood Plow Metab 14(2):217-26 (1994).

Schmid-Elsaesser R et al., "A critical reevaluation of the intraluminal thread model of focal cerebral ischemia. Evidence of inadvertent premature reperfusion and subarachnoid hemorrhage in rats by laser-Doppler flowmetry," Stroke 29:2162-2170 (1998).

Jolliet-Riant P, Tillement JP, "Drug transfer across the blood-brain barrier and improvement of brain delivery," Fundam. Clin. Pharmacol, 13, 16-25 (1999).

Syelaz J, Hara H, Pinard E, Mraovitch S, MacKenzie ET, Edvinsson L, "Effects of stimulation of the sphenopalatine ganglion on cortical blood flow in the rat," Journal of Cerebral Blood Flow and Metabolism, 8, 875-878 (1988).

Toda N et al., "Cerebral vasodilation induced by stimulation of the pterygopalatine ganglion and greater petrosal nerve in anesthetized monkeys," Neuroscience 96(2):393-398 (2000).

Varghese et al., "Endoscopic transnasal neurolytic sphenopalatine ganglion block for head and neck cancer pain," J Laryngol Otol 115(5):385-7 (2001).

Roman GC, "Cholinergic dysfunction in vascular dementia," Curr Psychiatry Rep 7(1):18-26 (2005).

Van Gijn J. et al., "Subarachnoid haemorrhage: diagnosis, causes and management," Brain 124:249-278 (2001).

Davis SM et al., "Advances in penumbra imaging with MR," Cerebrovasc Dis 17 Suppl 3:23-7 (2004).

Zausinger VS et al., "Neurological impairment in rats after transient middle cerebral artery occlusion: a comparative study under various treatment paradigms," Brain Research 863(1-2):94-105 (2000).

Phan TG et al., "Salvaging the ischaemic penumbra: more than just reperfusion?" Clin Exp Pharmacol Physiol 29(1-2):1-10 (2002).

Zhang ZG et el., "VEGF enhances angiogenesis and promotes blood-brain barrier leakage in the ischemic brain," J Clin Invest 106:829-838 (2000).

Kawamata T et al., "Intracisternal basic fibroblast growth factor (bFGF) enhances behavioral recovery following focal cerebral infarction in the rat," J Cereb Blood Flow Metab 16:542-547 (1996).

Ziche M et al., "Nitric oxide and angiogenesis," J Neurooncol 50:139-148 (2000).

Zhang R et al., "A nitric oxide donor induces neurogenesis and reduces functional deficits after stroke in rats," Ann Neurol 50:602-611 (2001).

De la Torre JC, "Vascular basis of Alzheimer's pathogenesis," Ann NY Acad Sci 977:196-215 (2002).

Hunter AJ et al., "To what extent have functional studies of ischemia in animals been useful in the assessment of potential neuroprotective agents?" Trends Pharmacol Sci 19:59-66 (1998).

Nollet H et al., "Transcranial magnetic stimulation: review of the technique, basic principles and applications," The Veterinary Journal 166:28-42 (2003).

Kanner AA et al., "Serum S100beta: a noninvasive marker of blood-brain barrier function and brain lesions," Cancer 97(11):2806-13 (2003).

Tony JFL, "Nitric oxide and the cerebral vascular function," J Biomed Sci 7:16-26 (2000).

Sandgren K et al., "Vasoactive intestinal peptide and nitric oxide promote survival of adult rat myenteric neurons in culture," J Neurosci Res 72(5):595-602 (2003).

Laude K et al., "NO produced by endothelial NO synthase is a mediator of delayed preconditioning-induced endothelial protection," Am J Physiol Heart Circ Physiol 284(6):H2053-60 (2003) (Epub Jan. 9, 2003).

Khan M et al., "S-Nitrosoglutathione reduces inflammation and protects brain against focal cerebral ischemia in a rat model of experimental stroke," J Cereb Blood Flow Metab 25(2):177-92 (2005).

Pluta RM, "Delayed cerebral vasospasm and nitric oxide: review, new hypothesis, and proposed treatment," Pharmacol Ther 105(1):23-56 (2005).

Reis DJ et al., "Electrical stimulation of cerebellar fastigial nucleus reduces ischemic infarction elicited by middle cerebral artery occlusion in rat," J Cereb Blood Flow Metab 11(5):810-8 (1991).

Devoghel JC, "Cluster headache and sphenopalatine block," Acta Anaesthesiol Belg., 32(1):101-7 (1981)—an abstract.

J.D. Wong et al., "Maxillary nerve block anaesthesia via the greater palatine canal: A modified technique and case reports", Australian Dental Journal, 1991;36(1):15-21.

Office Action dated Jun. 27, 2008, which issued during the prosecution of Applicants' U.S. Appl. No. 10/518,322.

An Office Action dated Feb. 17, 2009 which issued during the prosecution of Applicants' U.S. Appl. No. 11/668,305.

A Written Opinion dated Feb. 4, 2009, which issued during the prosecution of Applicants' PCT Patent Application No. PCT/IL03/00966.

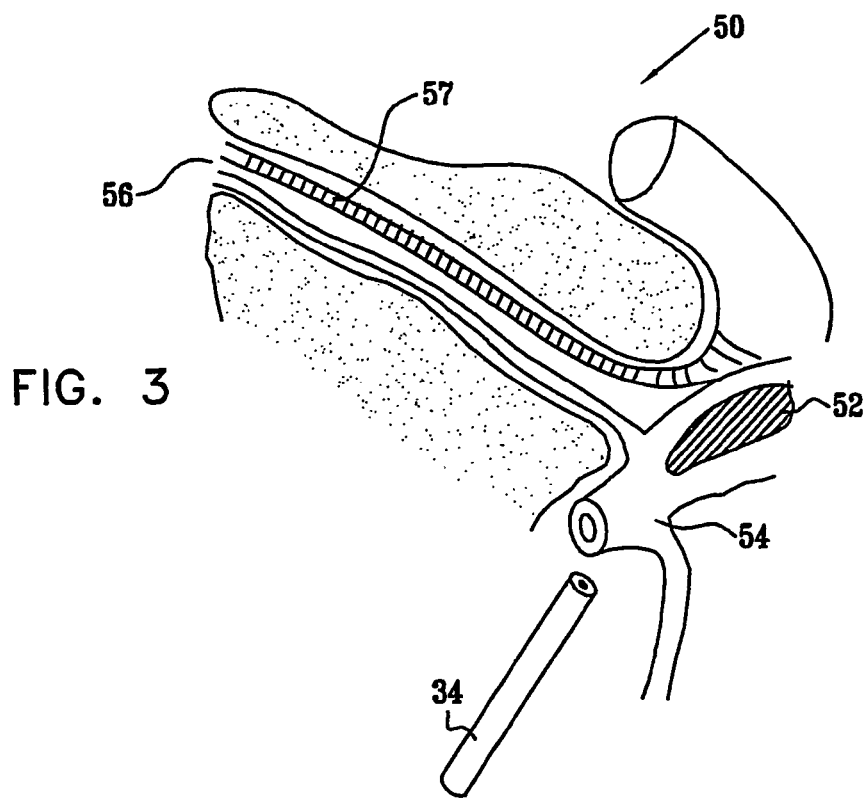
FIG. 3
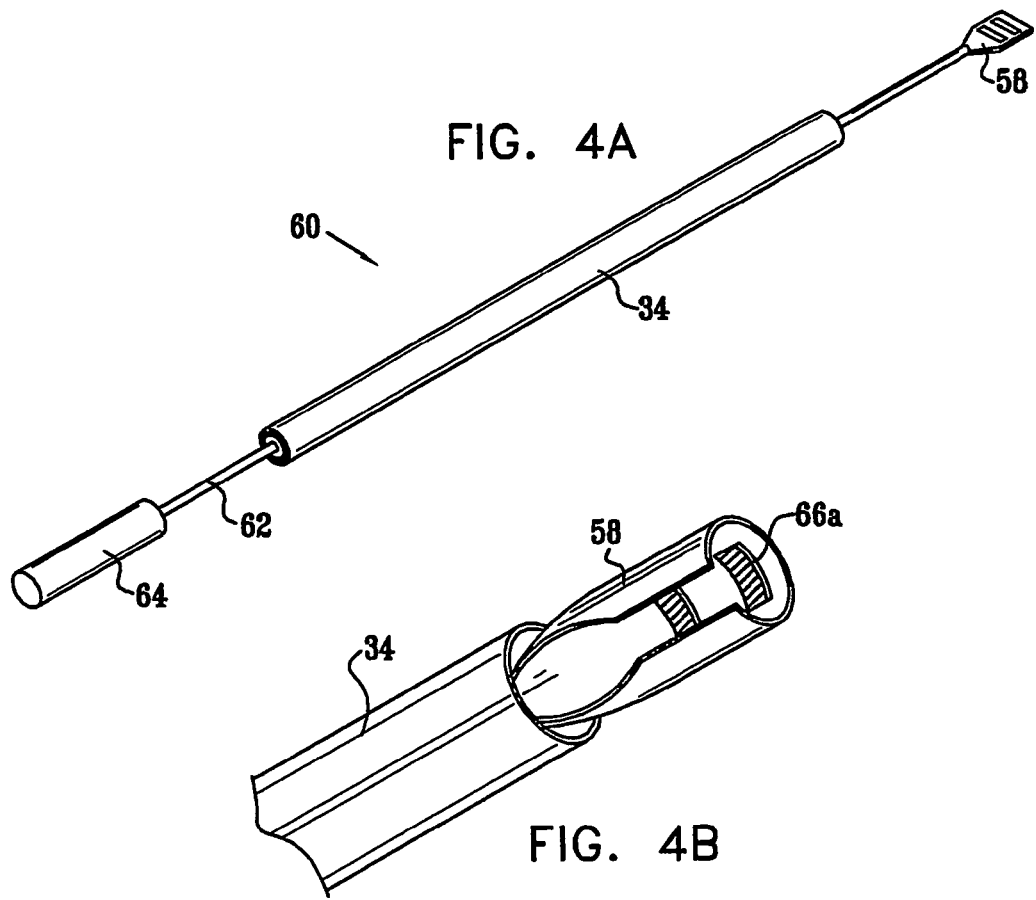
FIG. 4A
FIG. 4B

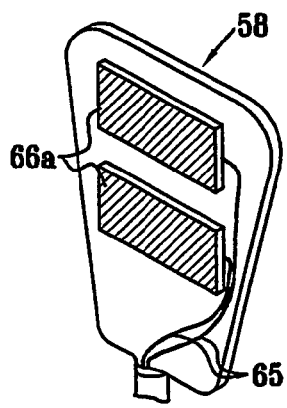
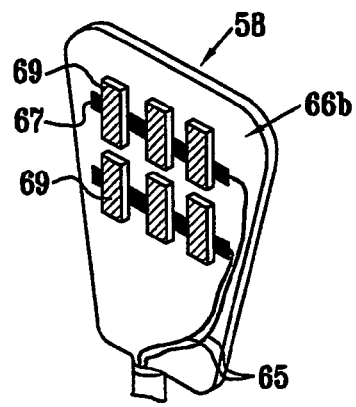
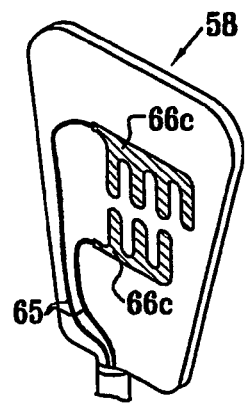
FIG. 5A  FIG. 5B  FIG. 5C
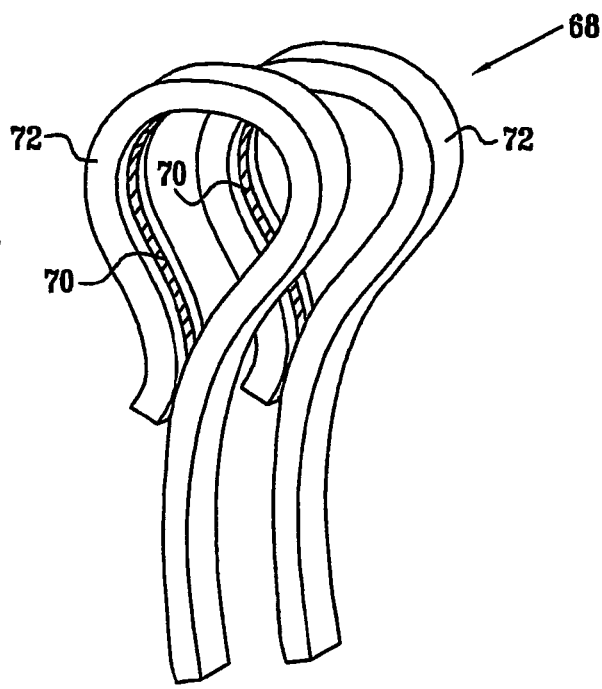
FIG. 6
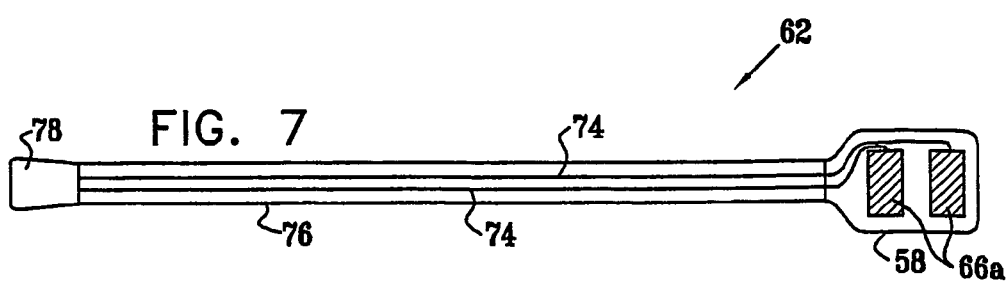
FIG. 7

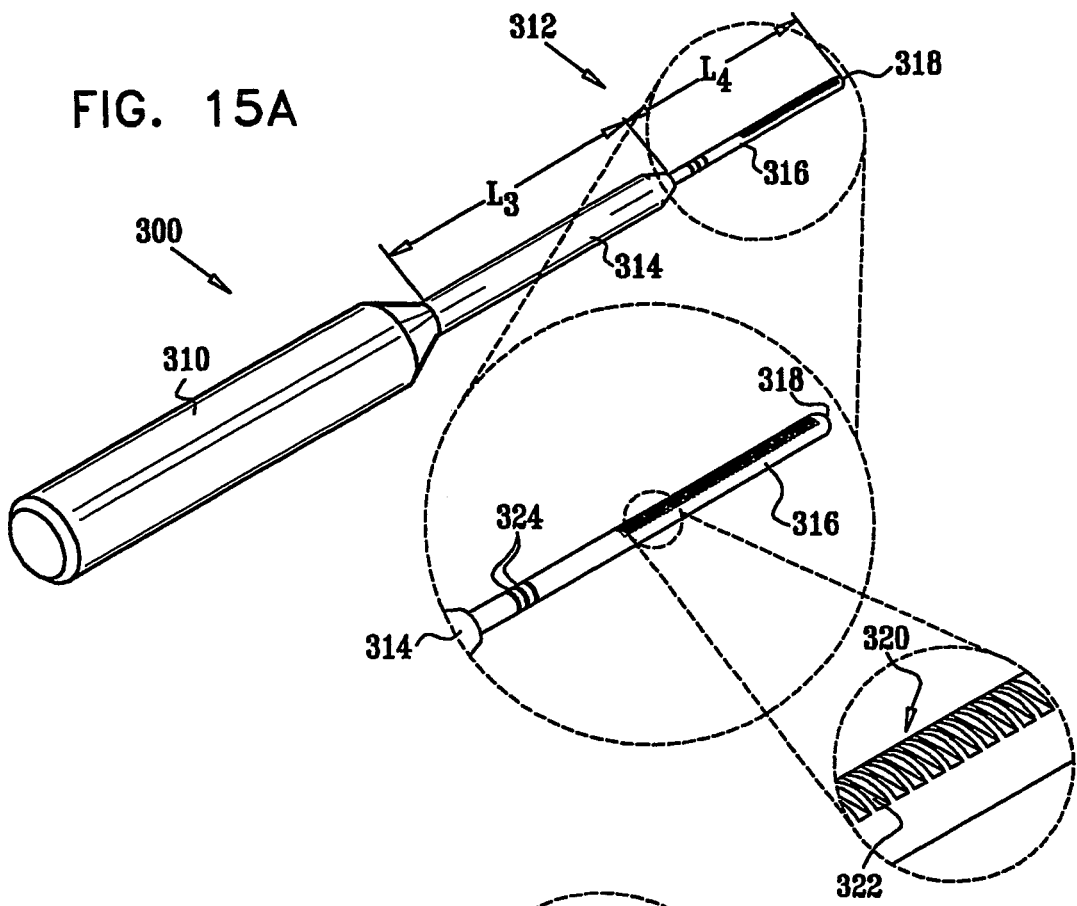
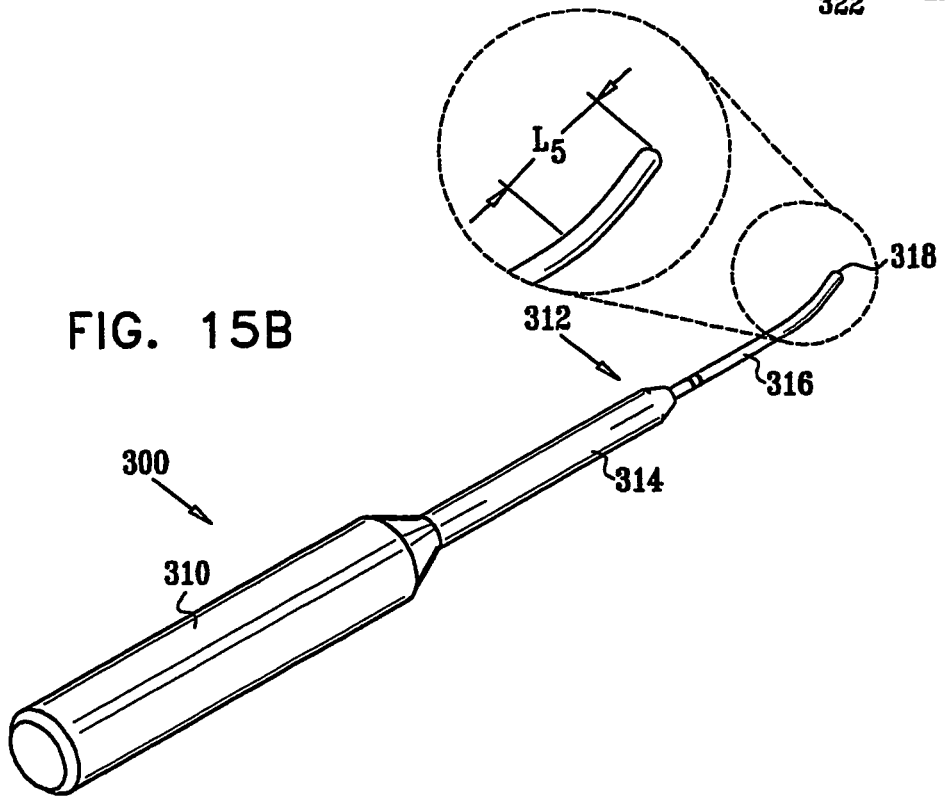
FIG. 15A
FIG. 15B

SURGICAL TOOLS AND TECHNIQUES FOR STIMULATION

CROSS-REFERENCES TO RELATED APPLICATIONS

This application claims priority from U.S. Provisional Patent Application 60/426,180, filed Nov. 14, 2002, entitled; "Surgical tools and techniques for stimulation," which is assigned to the assignee of the present application and is incorporated herein by reference.

FIELD OF THE INVENTION

The present invention relates generally to medical procedures and electronic devices. More specifically, the invention relates to the use of electrical devices for implantation in the head and surgical techniques for implanting the devices.

BACKGROUND OF THE INVENTION

The blood-brain barrier (BBB) is a unique feature of the central nervous system (CNS), which isolates the brain from the systemic blood circulation. To maintain the homeostasis of the CNS, the BBB prevents access to the brain for many substances circulating in the blood.

The BBB is formed by a complex cellular system of endothelial cells, astroglia, pericytes, perivascular macrophages, and a basal lamina. Compared to other tissues, brain endothelia have the most intimate cell-to-cell connections: endothelial cells adhere strongly to each other, forming structures specific to the CNS called "tight junctions" or zonula occludens. They involve two opposing plasma membranes, which form a membrane fusion with cytoplasmic densities on either side. These tight junctions prevent cell migration or cell movement between endothelial cells. A continuous uniform basement membrane surrounds the brain capillaries. This basal lamina encloses contractile cells called pericytes, which form an intermittent layer and probably play some role in phagocytosis activity and defense if the BBB is breached. Astrocytic end feet, which cover the brain capillaries, build a continuous sleeve and maintain the integrity of the BBB by the synthesis and secretion of soluble growth factors (e.g., gamma-glutamyl transpeptidase) essential for the endothelial cells to develop their BBB characteristics.

Because of the BBB, certain non-surgical treatments of the brain based upon systemic introduction of compounds through the bloodstream have been ineffective or less effective. For example, chemotherapy has been relatively ineffective in the treatment of CNS metastases of systemic cancers (e.g., breast cancer, small cell lung cancer, lymphoma, and germ cell tumors) despite clinical regression and even complete remission of these tumors in non-CNS systemic locations. The most important factors determining drug delivery from blood into the CNS are lipid solubility, molecular mass, and electrical charge. A good correlation exists between the lipid solubility of a drug, expressed as the octanol/water partition coefficient, and the drug's ability to penetrate or diffuse across the BBB. This is particularly relevant for drugs with molecular weights smaller than 600 Dalton (Da). The normal BBB prevents the passage of ionized water soluble drugs with molecular weight greater than 180 Da. Most currently available effective chemotherapeutic agents, however, have a molecular weight between 200 and 1200 Da Therefore, based both on their lipid solubilities and molecular masses, the passage of many agents is impeded by the BBB.

In addition to transcellular diffusion of lipophilic agents, there are several specific transport mechanisms to carry certain molecules across the brain's endothelial cells. Specific transport proteins exist for required molecules, such as glucose and amino acids. Additionally, absorptive endocytosis and transcytosis occur for cationized plasma proteins. Specific receptors for certain proteins, such as transferrin and insulin, mediate endocytosis and transport across the cell.

Non-surgical treatment of neurological disorders is generally limited to systemic introduction of compounds such as neuropharmaceuticals and other neurologically active agents that might remedy or modify neurologically related activities and disorders. Such treatment is limited, however, by the relatively small number of known compounds that pass through the BBB. Even those that do cross the BBB often produce adverse reactions in other parts of the body or in non-targeted regions of the brain There have been a number of different studies regarding efforts to cross the BBB, specifically with regard to overcoming the limited access of drugs to the brain. Such efforts have included, for example, chemical modification, development of more hydrophobic analogs, or linking an active compound to a specific carrier. Transient opening of the BBB in humans has been achieved by intracarotid infusion of hypertonic mannitol solutions or bradykinin analogs. Also, modulation of the P-glycoprotein, whose substrates are actively pumped out of brain cells into capillary lumens, has been found to facilitate the delivery of drugs to the brain.

The sphenopalatine ganglion (SPG) is a neuronal center located in the brain behind the nose. It consists of parasympathetic neurons innervating the middle cerebral and anterior cerebral lumens, the facial skin blood vessels, and the lacrimal glands. Activation of this ganglion is believed to cause vasodilation of these vessels. A second effect of such stimulation is the opening of pores in the vessel walls, causing plasma protein extravasation (PPE). This effect allows better transport of molecules from within these blood vessels to surrounding tissue.

The middle and anterior cerebral arteries provide the majority of the blood supply to the cerebral hemispheres, including the frontal and parietal lobes in their entirety, the insula and the limbic system, and significant portions of the following structures: the temporal lobes, internal capsule, basal ganglia and thalamus. These structures are involved in many of the neurological and psychiatric diseases of the brain. Currently the SPG is a target of manipulation in clinical medicine, mostly in attempted treatments of severe headaches, such as cluster headaches. The ganglion is blocked either on a short-term basis, by applying lidocaine, or permanently, by ablation with a radio frequency probe. In both cases the approach is through the nostrils.

The following references, which are incorporated herein by reference, may be useful:

Delepine, L., Aubineau, P., "Plasma protein extravasation induced in the rat dura mater by stimulation of the parasympathetic sphenopalatine ganglion," Experimental Neurology, 147,389-400 (1997).

Hara, H., Zhang, Q. J., Kuroyanagi, T., Kobayashi, S., "Parasympathetic cerebrovascular innervation: An anterograde tracing from the sphenopalatine ganglion in the rat," Neurosurgery, 32, 822-827 (1993).

Jolliet-Raint, P., Tillement, J. P., "Drug transfer across the blood-brain barrier and improvement of brain delivery," Fundam. Clin. Pharmacol., 13, 16-25 (1999).

Kroll, R. A., Neuwelt, E. A., "Outwitting the blood brain barrier for therapeutic purposes: Osmotic opening and other means," Neurosurgery, 42, 1083-1100(1998).

Sanders, M., Zuurmond, W. W., "Efficacy of sphenopalatine ganglion blockade in 66 patients suffering from cluster headache: A 12-70 month follow-up evaluation," Journal of Neurosurgery, 87, 876-880 (1997).

Seylaz, J., Hara, H., Pinard, E., Mraovitch, S., MacKenzie, E. T., Edvinsson, L, "Effects of stimulation of the sphenopalatine ganglion on cortical blood flow in the rat," Journal of Cerebral Blood Flow and Metabolism, 8, 875-878 (1988).

Van de Waterbeemd, H., Camenisch, G., Folkers, G., Chretien, J. R, Raevsky, O. A., "Estimation of blood brain barrier crossing of drugs using molecular size and shape and h bonding descriptors," Journal of Drug Targeting, 6, 151-165 (1998).

Suzuki, N., Hardebo, J. E., Kahrstrom, J., Owman, C., "Selective electrical stimulation of postganglionic cerebrovascular parasympathetic nerve fibers originating from the sphenopalatine ganglion enhances cortical blood flow in the rat," Journal of Cerebral Blood Flow and Metabolism, 10, 383-391 (1990).

Suzuki, N., Hardebo, J. E., Kahrstrom, J., Owrnan, C. H., "Effect on cortical blood flow of electrical stimulation of trigeminal cerebrovascular nerve fibres in the rat," Acta Physiol. Scand., 138, 307-315 (1990).

Branston N M, "The physiology of the cerebrovascular parasympathetic innervation," British Journal of Neurosurgery 9:319-329 (1995).

Branston N M et al., "Contribution of cerebrovascular parasympathetic and sensory innervation to the short-term control of blood flow in rat cerebral cortex," J Cereb Blood Flow Metab 15(3):525-31 (1995).

Toda N et al., "Cerebral vasodilation induced by stimulation of the pterygopalatine ganglion and greater petrosal nerve in anesthetized monkeys," Neuroscience 96(2):393-398 (2000).

Seylaz J et al., "Effect of stimulation of the sphenopalatine ganglion on cortical blood flow in the rat," J Cereb Blood Flow Metab 8(6):875-8 (1988).

PCT Patent Publication WO 01/85094 to Shalev and Gross, which is assigned to the assignee of the present patent application and whose disclosure is incorporated herein by reference, describes methods and apparatus for stimulating the sphenopalatine ganglion to modify properties of the blood brain barrier and cerebral blood flow for the treatment of medical conditions. Treatment is accomplished directly via stimulation of the sphenopalatine ganglion and/or indirectly by the facilitation of drug transport across the blood brain barrier via stimulation of the sphenopalatine ganglion.

U.S. Pat. No. 6,526,318 to Ansarinia and related PCT Patent Publication WO 01/97905 to Ansarinia, whose disclosure is incorporated herein by reference, describes a method for treating a patient by placing at least one electrode on or proximate to at least one of the patient's sphenopalatine ganglia, sphenopalatine nerves, or vidian nerves, and activating the electrode to apply an electrical signal and/or a medical solution to at least one of those ganglia or nerves. The '318 patent and '905 publication also describe surgical techniques for implanting the electrode via a coronoid notch of the patient U.S. Pat. No. 6,405,079 to Ansarinia, whose disclosure is incorporated herein by reference, describes methods for treating medical conditions by implanting one or more electrodes in regions of the sinus and applying electrical stimulation and/or medical solutions to the implantation site. The '079 patent also describes surgical techniques for implanting the electrode.

SUMMARY OF THE INVENTION

In some embodiments of the present invention, apparatus for stimulating the "sphenopalatine ganglion (SPG) system," as defined hereinbelow, is surgically implanted so as to stimulate the SPG system. Typically, the surgical procedure is performed in a relatively minimally-invasive manner to reduce patient discomfort during and after the procedure. Once implanted, the apparatus typically delivers the energy to the SPG system in order to control and/or modify SPG-related behavior, e.g., in order to induce changes in cerebral blood flow and/or to modulate permeability of the blood-brain-barrier (BBB). These embodiments may be used in many medical applications, such as, by way of illustration and not limitation, (a) the treatment of cerebrovascular disorders such as stroke, (b) the treatment of migraine headaches, (c) the treatment of Alzheimer's disease, (d) the facilitation of drug transport across the BBB, and/or (e) the facilitation of extraction of analytes from the brain.

In the present patent application, including the claims, "SPG system" means the SPG and associated neuroanatomical structures, including neural tracts originating in or reaching the SPG, including outgoing and incoming parasympathetic and sympathetic tracts, which tracts include preganglionic fibers of the SPG (fibers contained within the vidian nerve) and postganglionic fibers of the SPG (fibers that travel anterogradely from the SPG toward the brain vascular bed, including the anterior and posterior ethmoidal nerves, and including the retro-orbital branches of the SPG, which are fibers that connect the SPG with orbital neural structures).

It is to be appreciated that, in general, the techniques described herein may be applied directly, or applied with changes mutatis mutandis, so as to facilitate stimulation of one or more of the following and thereby facilitate treatment of a medical condition:

a sphenopalatine ganglion (SPG) (also called a pterygopalatine ganglion);
an anterior ethmoidal nerve;
a posterior ethmoidal nerve;
a communicating branch between the anterior ethmoidal nerve and the SPG (retro-orbital branch);
a communicating branch between the posterior ethmoidal nerve and the SPG (retro-orbital branch)
a nerve of the pterygoid canal (also called a vidian nerve), such as a greater superficial petrosal nerve (a preganglionic parasympathetic nerve) or a lesser deep petrosal nerve (a postganglionic sympathetic nerve);
a greater palatine nerve;
a lesser palatine nerve;
a sphenopalatine nerve;
a communicating branch between the maxillary nerve and the sphenopalatine ganglion;
a nasopalatine nerve;
a posterior nasal nerve;
an infraorbital nerve;
an otic ganglion;
an afferent fiber going into the otic ganglion; and/or
an efferent fiber going out of the otic ganglion.

According to some embodiments of the present invention, a method and apparatus are provided to facilitate placement of at least one electrode adjacent to the SPG via an endoscopic transpalatine approach to the SPG. Typically, local anesthetic is applied to the oral palatine mucosa and a greater palatine block is performed prior to a mucoperiosteal incision proximate the greater palatine foramen to reveal the contents of the foramen. A trocar comprising a flexible guide tube is typically inserted vertically through the incision to provide access for endoscopic dissection and visualization tools, which are used for the subsequent portion of the procedure. Typically, the endoscopic tools are used for subperiosteal dissection to detach the greater palatine canal contents from the osseous part of the canal and provide access to the vidian foramen and a portion of the SPG.

Typically, at least one electrode is placed next to or in contact with the SPG via the flexible guide tube. In an embodiment, each electrode is flat so as to provide a large contact area between the electrode and SPG. Typically, the electrode is flexible enough to be rolled up and inserted through the trocar and guide tube and sufficiently elastic to resume a generally planar shape once through the trocar and guide tube. Additionally or alternatively, the electrode has a curved shape such that it may be hooked around a nerve in the SPG system, such as the vidian nerve.

Typically, the at least one electrode comprises two or more electrodes, driven to operate in a multi-polar mode (e.g., in a bipolar mode for the case of two electrodes).

According to some embodiments of the present invention, a method and apparatus are provided to facilitate placement of at least one electrode adjacent to the SPG via a transpalatine approach to the SPG. The area of the greater palatine foramen is anesthetized, and a full-thickness mucogingival incision is performed at the midline of the hard palate, including about 0.5 cm of the soft palate. Two releasing incisions are performed at the ends of the midline incision. A mucoperiosteal flap is raised, and the greater palatine neurovascular bundle is carefully exposed, revealing the contents of the greater palatine foramen. A stylet is inserted posteriorly through the greater palatine canal to the greater palatine neurovascular bundle, and supported against the posterior wall of the greater palatine canal. The stylet is removed, and a series of passive tip periosteal elevators, having successively greater distal shaft diameters, is used to widen the path created using the stylet.

An introducer is provided for introducing a neural stimulator into the greater palatine canal. The introducer typically comprises a handle for manipulating the introducer, a rod, and a protective sleeve. The neural stimulator typically comprises an electrode support, a receiver, and a connecting tube. The electrode support is mounted on the introducer by fitting the protective sleeve of the introducer over the electrode support. During the surgical procedure, after the greater palatine canal has been widened, the introducer is inserted into the greater palatine canal, and a surface of the stimulator that comprises at least one electrode is placed in contact with the posterior aspect of the sphenopalatine ganglion.

Subsequent to placement of the at least one electrode, proper placement is typically assured by running a test current through the at least one electrode and monitoring the physiological effect on the patient. Typically, once proper placement of the at least one electrode is assured, the at least one electrode is coupled to a control unit. For some applications, the control unit is implanted in the patient. Alternatively, an external control unit is used to control the at least one electrode.

According to some embodiments of the present invention, a method and apparatus are provided to facilitate placement of at least one electrode adjacent to the SPG via a combined trans-maxillary sinus and trans-nasal endoscopic assisted approach. Typically, after administration of appropriate anesthesia, the posterior wall of the maxillary sinus is carefully dissected and the anterior part of the sphenopalatine fossa is dissected via a trans-maxillary approach. The dissection is typically performed approximately 0.5 mm from the medial wall of the maxillary sinus, under direct endoscopic visualization. Subsequently, a complete nasal endoscopic examination is typically performed on both sides, and then, under direct visualization, an incision is made about 0.4 mm—about 0.8 mm under the second conchae on the operating side. Typically, a mucoperiosteal flap is raised posteriorly and inferiorly, to allow the sphenopalatine artery to be dissected and clamped. The sphenopalatine fossa is then typically approached under direct endoscopic visualization, and the lateral wall of the nose is penetrated. Subsequently, in an embodiment, the SPG is approached via the maxillary sinus. In another embodiment, the SPG is accessed via a trans-nasal approach.

Typically, an introducer, comprising a hollow tube, is inserted through the dissected tissue to provide a pathway for introduction of the at least one electrode, which comprises a lead wire, to a region adjacent to the SPG. In an embodiment the electrodes are flat, such that a large surface area is available for contact with the SPG. In another embodiment, one or more of the electrodes are curved, so as to wrap around a portion of a nerve such as the vidian nerve, or another nerve in the SPG system.

Once the at least one electrode is placed, a controlled stimulation is typically performed by passing a current through the lead wire to the electrode to confirm that the electrode is properly placed. Evaluation of the proper placement of the at least one electrode comprises one or more of: (1) evaluating the vasodilatation of blood vessels in the eye, (2) assessment of cerebral blood flow by using a transcranial Doppler, (3) assessment of forehead perfusion by using Laser Doppler, and (4) assessment of forehead perfusion by a temperature sensor. In an embodiment, once proper placement of the electrodes has been verified, the electrodes are coupled to an implantable control unit. In another embodiment, the electrodes are coupled to an external control unit by wired or wireless means.

There is therefore provided, in accordance with an embodiment of the present invention, apparatus for treating a subject, including:

a stimulation device, adapted to be implanted in a vicinity of a site selected from the list consisting of: a sphenopalatine ganglion (SPG) of the subject and a neural tract originating in or leading to the SPG; and a connecting element, coupled to the stimulation device, and adapted to be passed through at least a portion of a greater palatine canal of the subject.

In an embodiment, the portion of the greater palatine canal has a length of at least about 2 cm, and the connecting element is adapted to be passed through the portion.

In an embodiment, the connecting element includes at least one mark, adapted to indicate a depth of insertion of the stimulation device in the greater palatine canal.

In an embodiment, the stimulation device is adapted to stimulate the site, and to configure the stimulation to be sufficient to induce a change in cerebral blood flow of the subject In an embodiment, the stimulation device is adapted to stimulate the site, and to configure the stimulation to be sufficient to modulate permeability of a blood-brain-barrier of the subject.

In an embodiment, the site includes the SPG of the subject, and the stimulation device is adapted to be implanted in the vicinity of the SPG.

In an embodiment, the site includes a vidian nerve of the subject, and the stimulation device is adapted to be implanted in the vicinity of the vidian nerve.

In an embodiment, the site includes an ethmoidal nerve of the subject, and the stimulation device is adapted to be implanted in the vicinity of the ethmoidal nerve.

In an embodiment, the site includes a retro-orbital branch of the SPG of the subject, and the stimulation device is adapted to be implanted in the vicinity of the retro-orbital branch.

In an embodiment, the apparatus includes an introducer, adapted for mounting the stimulation device thereon, and to be passed through the at least a portion of the greater palatine canal.

In an embodiment, the stimulation device includes at least one electrode. For example, the electrode may be configured to wrap around a nerve of the subject in the vicinity of the site.

In an embodiment, the apparatus includes a stimulator, coupled to the connecting element, and adapted to be fixed to a hard palate of the subject. For example, the stimulator may be adapted to be coupled to the hard palate in a supraperiosteal region thereof. For some applications, the stimulator is adapted to be coupled to an upper surface of the hard palate in a nasal cavity of the subject. For some applications, the stimulator is adapted to be coupled to a lower surface of the hard palate.

There is further provided, in accordance with an embodiment of the present invention, apparatus for insertion into a greater palatine canal of a subject, including a stylet, which includes:

a proximal rod shaft, having a first diameter; and a distal rod shaft, having a second diameter less than the first diameter, such that a region between the proximal rod shaft and the distal rod shaft is shaped so as to define a shoulder which is adapted to prevent insertion of the distal rod shaft into a sphenopalatine fossa of the subject beyond a depth of the greater palatine canal.

In an embodiment, the distal rod shaft includes a cutting implement, located in a vicinity of a distal tip of the shaft.

In an embodiment, the proximal rod shaft has a length of between about 20 mm and about 150 mm.

In an embodiment, the first diameter is between about 1.5 mm and about 6 mm.

In an embodiment, the distal rod shaft has a length of between about 3 mm and about 20 mm.

In an embodiment, the second diameter is between about 1 mm and about 1.5 mm.

In an embodiment, the apparatus includes a periosteal elevator for insertion into the greater palatine canal, the elevator including at least one mark adapted to indicate a depth of insertion of the periosteal elevator in the greater palatine canal.

There is still further provided, in accordance with an embodiment of the present invention, apparatus for insertion into a greater palatine canal of a subject, including a periosteal elevator, which includes at least one mark adapted to indicate a depth of insertion of the periosteal elevator in the greater palatine canal.

There is also provided, in accordance with an embodiment of the present invention, a method for implanting a treatment stimulation device in a vicinity of a site of a subject, including:

passing the device through a greater palatine foramen of the subject; and bringing the device into contact with the vicinity of the site, the site selected from the list consisting of: a sphenopalatine ganglion (SPG) of the subject and a neural tract originating in or leading to the SPG.

There is also provided, in accordance with an embodiment of the present invention, a method for implanting a treatment stimulation device in a vicinity of a site of a subject, including:

passing the device through at least a portion of a greater palatine canal of the subject; and bringing the device into contact with the vicinity of the site, the site selected from the list consisting of: a sphenopalatine ganglion (SPG) of the subject and a neural tract originating in or leading to the SPG.

For some applications, the site includes the SPG of the subject, and bringing the device into contact with the vicinity of the site includes bringing the device into contact with the vicinity of the SPG.

For some applications, the site includes a vidian nerve of the subject, and bringing the device into contact with the vicinity of the site includes bringing the device into contact with the vicinity of the vidian nerve.

For some applications, the site includes an ethmoidal nerve of the subject, and bringing the device into contact with the vicinity of the site includes bringing the device into contact with the vicinity of the ethmoidal nerve.

For some applications, the site includes a retro-orbital branch of the SPG of the subject, and bringing the device into contact with the vicinity of the site includes bringing the device into contact with the retro-orbital branch.

For some applications, bringing the device into contact includes:

applying stimulation with the device;

observing one or more physiological responses of the subject to the stimulation; and verifying desired placement of the device responsive to the observation.

For some applications, bringing the device into contact includes applying stimulation with the device, and configuring the stimulation to be sufficient to induce a change in cerebral blood flow of the subject. For some applications, bringing the device into contact includes applying stimulation with the device, and configuring the stimulation to be sufficient to modulate permeability of a blood-brain-barrier of the subject.

For some applications, the stimulation device includes at least one electrode, and bringing the device into contact includes bringing the electrode into contact with the vicinity of the site. For some applications, bringing the electrode into contact includes wrapping the electrode around a nerve of the subject in the vicinity of the site.

For some applications, the stimulation device includes a stimulator, the method including fixing the stimulator to a hard palate of the subject For example, fixing the stimulator to the hard palate may include coupling the stimulator to a supraperiosteal region of the hard palate. In an embodiment, fixing the stimulator to the hard palate includes coupling the stimulator to an upper surface of the hard palate in a nasal cavity of the subject. In an embodiment, fixing the stimulator to the hard palate includes coupling the stimulator to a lower surface of the hard palate.

In an embodiment, passing the device through the greater palatine foramen includes determining a depth of insertion of the device in a greater palatine canal of the subject by observing at least one mark on the device indicative of the depth of the insertion.

In an embodiment, passing the device through the greater palatine foramen includes widening a greater palatine canal of the subject using a series of periosteal elevators having successively greater diameters.

In an embodiment, passing the device through the greater palatine foramen includes widening a greater palatine canal of the subject using a series of tools having successively greater diameters.

In an embodiment, passing the device through the greater palatine foramen includes mounting the device on an introducer, and passing the introducer through the greater palatine foramen.

In an embodiment, passing the device through the portion of the greater palatine canal includes determining a depth of insertion of the device in the greater palatine canal by observing at least one mark on the device indicative of the depth of the insertion.

In an embodiment, passing the device through the at least a portion of the greater palatine canal includes passing the device through at least about 2 cm of the greater palatine canal.

In an embodiment, passing the device through the at least a portion of the greater palatine canal includes widening the portion using a series of periosteal elevators having successively greater diameters.

In an embodiment, passing the device through the at least a portion of the greater palatine canal includes widening the portion using a series of tools having successively greater diameters.

In an embodiment, passing the device through the at least a portion of the greater palatine canal includes mounting the device on an introducer, and passing the introducer through the portion.

There is yet additionally provided, in accordance with an embodiment of the present invention, a method for implanting a treatment device in a vicinity of a site of a subject, including:

passing the device through a trans-maxillary sinus of the subject; and bringing the device into contact with the vicinity of the site, the site selected from the list consisting of: a sphenopalatine ganglion (SPG) of the subject and a neural tract originating in or leading to the SPG.

In an embodiment, the site includes the SPG of the subject, and bringing the device into contact with the vicinity of the site includes bringing the device into contact with the vicinity of the SPG.

In an embodiment, the site includes a vidian nerve of the subject, and bringing the device into contact with the vicinity of the site includes bringing the device into contact with the vicinity of the vidian nerve.

In an embodiment, the site includes an ethmoidal nerve of the subject, and bringing the device into contact with the vicinity of the site includes bringing the device into contact with the vicinity of the ethmoidal nerve.

In an embodiment, the site includes a retro-orbital branch of the SPG of the subject, and bringing the device into contact with the vicinity of the site includes bringing the device into contact with the retro-orbital branch.

In an embodiment, bringing the device into contact includes:

applying stimulation with the device;

observing one or more physiological responses of the subject to the stimulation; and verifying desired placement of the device responsive to the observation.

There is still additionally provided, in accordance with an embodiment of the present invention, a method for implanting a treatment device in a vicinity of a site of a subject, including:

passing the device through a sphenopalatine foramen canal of the subject; and bringing the device into contact with the vicinity of the site, the site selected from the list consisting of a sphenopalatine ganglion (SPG) of the subject and a neural tract originating in or leading to the SPG.

In an embodiment, the site includes the SPG of the subject, and bringing the device into contact with the vicinity of the site includes bringing the device into contact with the vicinity of the SPG.

In an embodiment, the site includes a vidian nerve of the subject, and bringing the device into contact with the vicinity of the site includes bringing the device into contact with the vicinity of the vidian nerve.

In an embodiment, the site includes an ethmoidal nerve of the subject, and bringing the device into contact with the vicinity of the site includes bringing the device into contact with the vicinity of the ethmoidal nerve.

In an embodiment, the site includes a retro-orbital branch of the SPG of the subject, and bringing the device into contact with the vicinity of the site includes bringing the device into contact with the retro-orbital branch.

In an embodiment, bringing the device into contact includes:

applying stimulation with the device;

observing one or more physiological responses of the subject to the stimulation; and verifying desired placement of the device responsive to the observation.

There is also provided, in accordance with an embodiment of the present invention, a method for implanting a treatment device in a vicinity of an ethmoidal nerve of a subject, including:

passing the device through an ethmoidal foramen of the subject; and bringing the device into contact with the vicinity of the ethmoidal nerve.

In an embodiment, the ethmoidal nerve includes an anterior ethmoidal nerve of the subject, and bringing the device into contact includes bringing the device into contract with the vicinity of the anterior ethmoidal nerve.

In an embodiment, the ethmoidal nerve includes a posterior ethmoidal nerve of the subject, and bringing the device into contact includes bringing the device into contract with the vicinity of the posterior ethmoidal nerve.

In an embodiment, bringing the device into contact includes:

applying stimulation with the device;

observing one or more physiological responses of the subject to the stimulation; and verifying desired placement of the device responsive to the observation.

The present invention will be more fully understood from the following detailed description of the embodiments thereof, taken together with the drawings in which:

BRIEF DESCRIPTION OF THE DRAWINGS

FIG. 3 is a pictorial illustration of an endoscopic tool accessing the SPG system, in accordance with an embodiment of the present invention;

FIGS. 4A and 4B are schematic illustrations of an electrode introducer for placing an electrode in the SPG system, in accordance with an embodiment of the present invention;

FIGS. 5A, 5B, and 5C are schematic illustrations of electrode supports to be placed in the SPG system, in accordance with embodiments of the present invention;

FIG. 6 is a schematic illustration of an electrode to be hooked around a nerve in the SPG system, in accordance with an embodiment of the present invention;

FIG. 7 is a schematic illustration of an endoscopic tool for placing an electrode in the SPG system, in accordance with an embodiment of the present invention;

FIGS. 15A and 15B are schematic illustrations of a passive tip periosteal elevator used to widen the path created using the stylet of FIG. 13, in accordance with embodiments of the present invention;

DETAILED DESCRIPTION OF EMBODIMENTS

Figure 1:
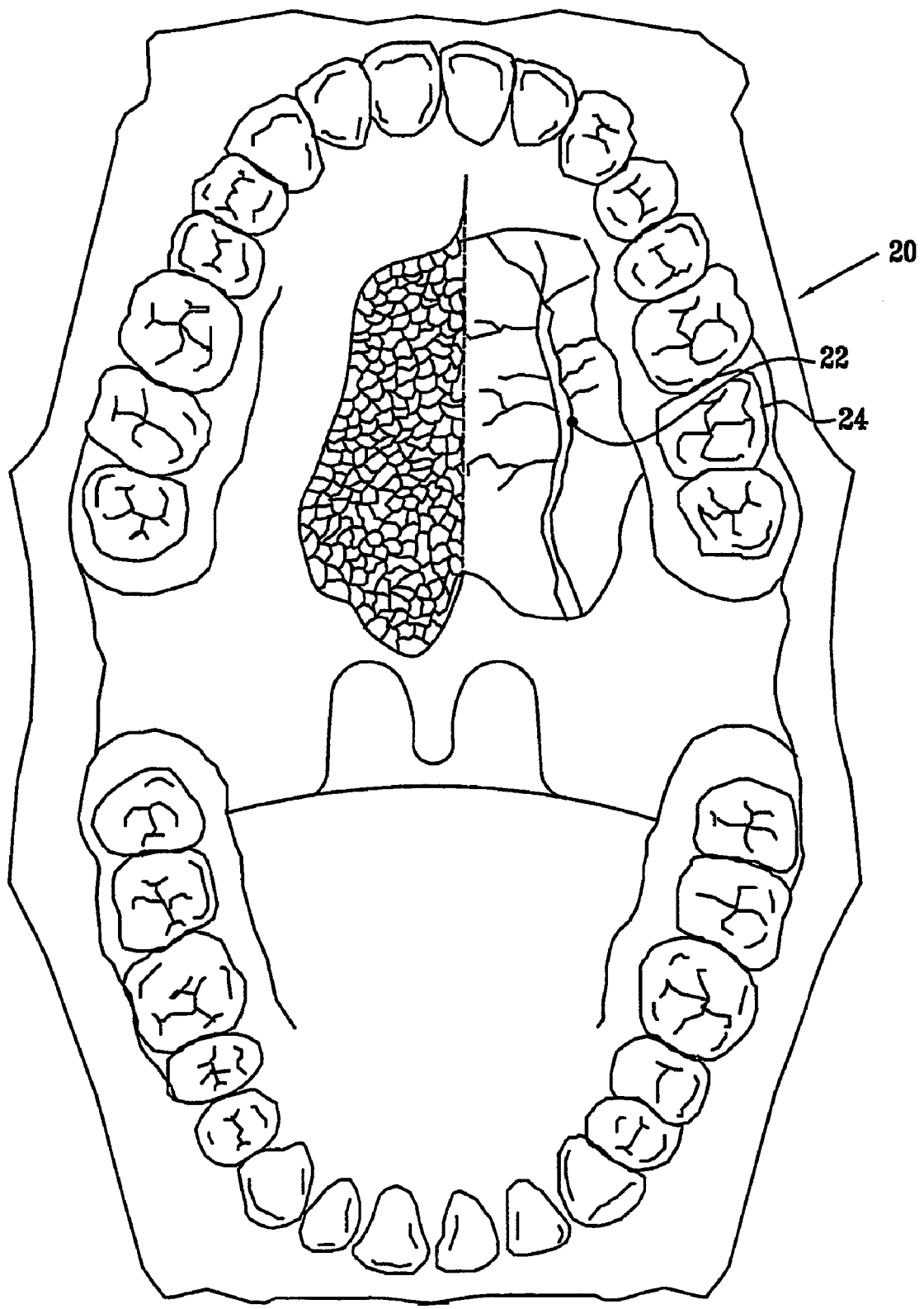
FIG. 1 is a pictorial illustration of the roof of the oral cavity, showing a site for an incision, in accordance with an embodiment of the present invention.

FIG. 1 is a schematic, pictorial illustration showing a roof of an oral cavity 20 and associated anatomical structures, where dissection commences in a surgical procedure to access the sphenopalatine ganglion (SPG) system, in accordance with an embodiment of the present invention. In this embodiment, soft tissue is dissected to expose a greater palatine foramen 22, in order to allow access via the greater palatine canal (also known as the pterygopalatine canal) to the SPG system by means of an endoscopic transpalatine approach.

To start the procedure, the patient is typically positioned with an open mouth, and a topical and local anesthetic is applied to the oral palatine mucosa Typically, after the local anesthetic has taken the desired effect (typically after about 2-3 minutes), a greater palatine nerve block is performed. Greater palatine foramen 22 is then located, typically by the anatomical landmark of a second upper molar 24. Typically, a mucoperiosteal incision is made in front of the location of greater palatine foramen 22, and the contents of the foramen are dissected and revealed.

Figure 2:
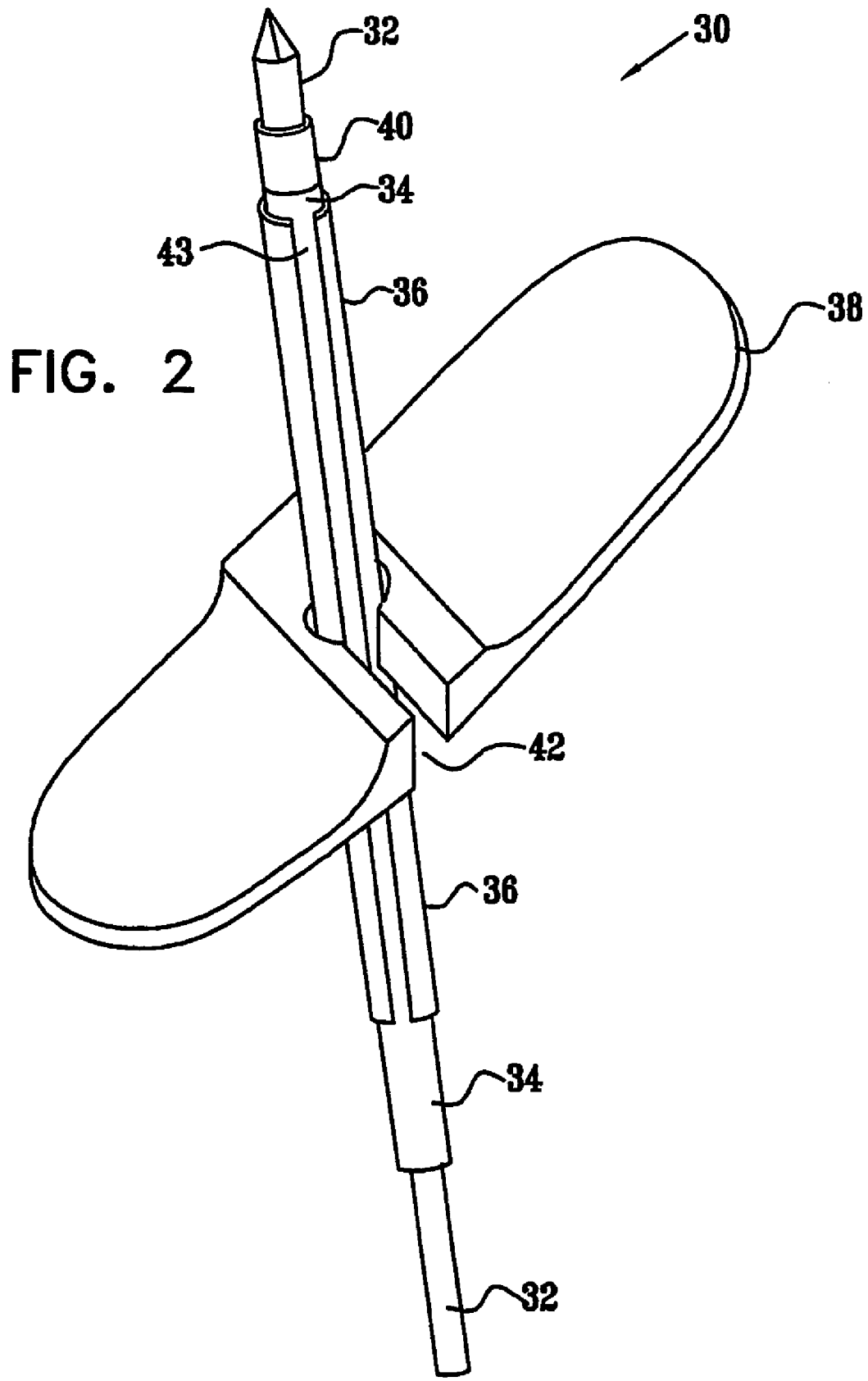
FIG. 2 is a schematic illustration of endoscopic apparatus for accessing the sphenopalatine ganglion (SPG) system, in accordance with an embodiment of the present invention.

FIG. 2 is a schematic illustration showing endoscopic apparatus 30, which is used in the surgical procedure to access the SPG once the contents of greater palatine foramen 22 have been dissected and revealed, in accordance with an embodiment of the present invention. Apparatus 30 comprises a handle 38, which contains a keyhole opening 42, through which a flexible hollow sleeve 36 is placed. Typically sleeve 36 serves as a conduit and guide for introduction of endoscopic tools, while handle 38 is used to move and orient sleeve 36 and any introduced endoscopic tools. Further typically, sleeve 36 comprises a slit 43, running the length of the sleeve, which is lined up with keyhole opening 42, such that handle 38 and sleeve 36 can be removed from around wires subsequently introduced through the sleeve.

In some embodiments of the present invention, hollow sleeve 36 is adapted to permit a flexible shaft 34 to be introduced and advanced to a desired operative site. Flexible shaft 34 is typically adapted such that a surgical tool 40 may be attached to the distal end of the shaft. For example, FIG. 2 shows a surgical tool comprising a periosteal elevator. In some embodiments of the present invention, flexible shaft 34 is hollow so as to allow the introduction of additional apparatus to the operative site. FIG. 2 shows an embodiment in which a trocar 32 is introduced through hollow flexible shaft 34.

Typically, endoscopic apparatus 30 is used to proceed with the surgical procedure subsequent to dissection of the contents of the greater palatine foramen, by inserting hollow sleeve 36 into the greater palatine foramen with the aid of handle 38. Once the hollow sleeve is suitably positioned, flexible shaft 34 with attached surgical tool 40 and trocar 32 are typically inserted through hollow sleeve 36. In an embodiment, surgical tool 40 comprises a periosteal elevator. Trocar 32 is typically advanced using a gentle 180 degree axial rotation, and subperiosteal dissection is performed with the aide of surgical tool 40 so as to detach the contents of the greater palatine canal from the osseous portion of the canal. Typically, the dissection is monitored with endoscopic visualization, while irrigation and suction are used as necessary to maintain the site of dissection. Trocar 32 should typically be introduced about 2 centimeters relative to the bony entrance of the greater palatine canal, with allowable variation for the anatomy of individual patients.

FIG. 3 illustrates shaft 34 and the anatomy of the pterygopalatine fossa 50, which shows an SPG 52 adjacent to a sphenopalatine artery 54, in accordance with an embodiment of the present invention. The pterygopalatine fossa is a bilateral intraosseous space at the craniofacial junction. Because of its location, it is considered together with the structures of the paranasal sinuses. The fossa resembles a four-sided pyramid with an imaginary base, anterior, posterior and medial wall all converging at the vertex. The base corresponds to the region of the orbital vertex. The anterior wall is bordered by a small vertical portion of the maxillary tuberosity close to its junction with the palatine vertical plate. The medial wall is formed by the vertical plate of the palatine bone and is crossed by the sphenopalatine foramen. The posterior wall corresponds to the anterior face of the pterygoid process of the sphenoid bone. The lateral wall lies against the skull, sealed by fibrous tissue, and allows the passage of the vascular and nervous structures. The vertex of the pyramid is the junction of the walls, where the palatine osseous canals connect the pterygopalatine fossa with the oral cavity through the hard palate.

A vidian nerve 57, contained in a vidian foramen 56, is seen to be connected to SPG 52. Typically, the vidian foramen and nerve are approached under direct endoscopic visualization, after the steps described hereinabove with reference to FIG. 2. Typically, hollow flexible shaft 34 (see also FIG. 2) is introduced towards vidian nerve 57 and/or SPG 52.

FIG. 4A shows an electrode introducer 60, comprising a flexible rod 62, to which an electrode support 58 is attached, and a handle 64 for manipulating the introducer, in accordance with an embodiment of the present invention. Typically, electrode support 58 is introduced to the region of the vidian nerve and the SPG via flexible shaft 34.

FIG. 4B shows flexible electrode support 58, rolled to fit inside shaft 34, at a point in time as support 58 is advanced out from shaft 34, such that support 58 opens upon exiting the distal end of shaft 34, in accordance with an embodiment of the present invention. Electrodes, such as plate electrodes 66a, described hereinbelow with reference to FIG. 5A, are affixed to one or more sites on the electrode support, and are positioned to be in contact with a target site such as the SPG when the support unrolls.

FIGS. 5A, 5B, and 5C show several electrode configurations for use with electrode support 58, in accordance with respective embodiments of the present invention. The three illustrated electrode configurations are typically flat, providing a relatively large surface area for contact with the SPG or other tissue. Additionally, the flexibility and flat thin shapes of the electrode support and the electrodes are conducive to being rolled up, for some applications, so as to fit through flexible shaft 34 and subsequently return to essentially their initial flat shape (see FIG. 4B). FIG. 5A shows a simple plate electrode design comprising two plate electrodes 66a, which are each connected to respective leads 65, typically but not necessarily by laser welding. Other embodiments comprise more than two plate electrodes 66a. Typically, plate electrodes 66a comprise platinum/iridium or other suitable substances known in the art of tissue stimulation.

FIG. 5B shows an alternate electrode design where each of two compound plate electrodes 66b typically comprises a horizontal strip 67, to which a plurality of vertical plates 69 is coupled. Typically, each horizontal strip 67 is coupled to a respective lead 65 by laser welding. Horizontal strip 67 and vertical plates 69 typically comprise platinum/iridium or other suitable substances known in the art of tissue stimulation.

FIG. 5C shows another electrode design providing a large surface area for contact with the SPG, comprising two shaped electrodes 66c, which are shaped to provide the desired electrical stimulation to the SPG. In an embodiment, electrodes 66c are formed by cutting the shapes out of a simple plate comprising platinum/iridium or other suitable substances known in the art of tissue stimulation.

For some applications, electrode support 58 shown in FIGS. 5A, 5B, and 5C is about 4 mm by about 6-10 mm. The total contact surface area between the SPG (or other tissue) and the electrodes in the embodiments shown in these figures is, for some applications, between about 0.5 mm$^2$ and about 2 mm$^2$.

FIG. 6 shows an electrode 68 that is configured to wrap around a nerve, in accordance with an embodiment of the present invention. Electrode 68 is shown in the figure in a bipolar configuration, for placement at respective longitudinal sites on the nerve. For some applications, electrode 68 comprises a single monopolar "hook" electrode. Typically, electrode 68 comprises two conductive strips 70, pre-bent to a curved shape such that they can be placed during a procedure to wrap around a target nerve, for example the vidian or ethmoidal nerves. The inner portion of conductive strips 70 is designated to be in contact with the target nerve (or only slightly separated therefrom), and provides the electrical stimulation to the nerve. The outer surfaces of strips 70, i.e., those surfaces not in contact with the nerve, are typically sheathed or otherwise coated in a non-conductive material 72, to reduce or eliminate stimulation of tissues surrounding the target nerve.

FIG. 7 shows details of flexible rod 62 (see FIGS. 4A and 4B), which is used in the placement of electrode support 58 and comprises one or more electrical leads 74 for transmitting electrical power to the electrodes (e.g., electrodes 66a, 66b, or 66c) on electrode support 58, in accordance with an embodiment of the present invention. Typically, electrical leads 74 are cast into a solid elastomer sheathing 76 to provide a desired degree of flexibility and strength during the introduction of the electrodes, and to also provide the isolation of the leads from bodily tissues and fluids.

Figure 8:
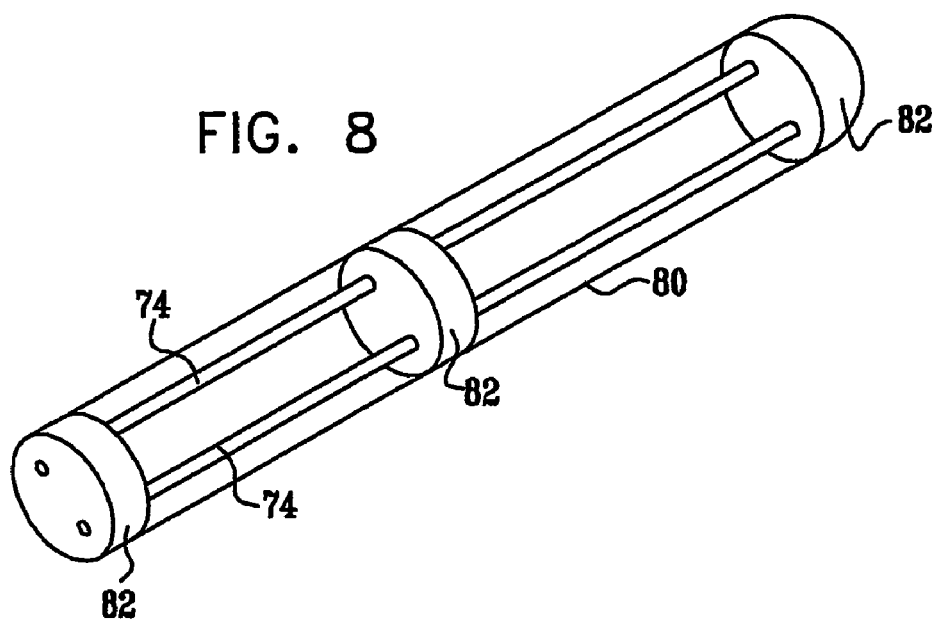
FIG. 8 is a schematic illustration of a system for supporting electrical leads during placement of an electrode in the SPG system, in accordance with an embodiment of the present invention.

FIG. 8 shows apparatus for supporting and protecting electrical leads 74 while maintaining sufficient strength and flexibility, in accordance with an embodiment of the present invention. Typically, leads 74 are threaded through a hollow tube 80, chosen to provide appropriate strength and flexibility, which typically comprises a plurality of supports 82 along the length of tube 80 for holding leads 74 and preventing damage to the leads during introduction or operation of the electrodes.

Figure 9A:
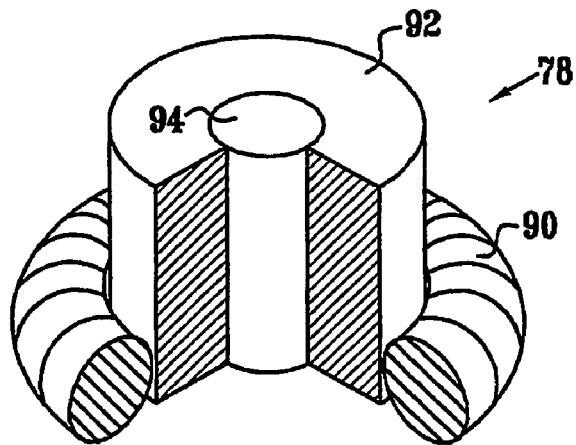
FIGS. 9A and 9B are schematic, partially sectional illustrations of receivers for receiving control and power signals to drive an electrode that is placed in the SPG system, in accordance with embodiments of the present invention.

FIG. 9A shows a partially sectional view of a receiver 78, which is adapted to be coupled to the proximal end of rod 62 (FIG. 4A) by a base 92 and to receive power and control signals from a control unit that drives electrodes, such as electrodes 66a, 66b, or 66c, on electrode support 58, in accordance with an embodiment of the present invention. Receiver 78 comprises a coil 90 and an electronics pod 94, which are coupled to a base 92 and adapted to receive power and drive the electrodes. Typically, coil 90 is constructed using Drawn Filled Tube technology, and typically comprises a combination of MP35N and silver. In an embodiment, coil 90 is adapted to receive control and power inputs wirelessly. By way of example but not limitation, RF electromagnetic fields and/or oscillating magnetic fields are used to wirelessly power and control the electrodes via coil 90 and electronics pod 94.

Figure 9B:
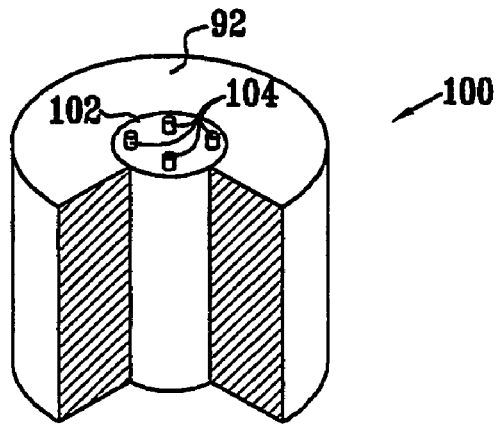

FIG. 9B shows a partially sectional view of a receiver 100, which is adapted to be coupled to the proximal end of rod 62 (FIG. 4A) by a base 92 and to receive power and control signals from a control unit that drives electrodes, such as electrodes 66a, 66b, or 66c, on electrode support 58, in accordance with an embodiment of the present invention. Receiver 100 comprises an electronics module 102, which comprises a plurality of connectors 104 for wired connections to a typically non-implanted control unit.

Typically, receivers 78 and 100 are coated with a non-permeable coating such as, but not limited to, Parylene, which isolates the receiver from physiological fluids and tissues.

Further typically, the receivers are encased in a relatively pliant layer such as an elastomer, which serves as an outer casing for the receiver.

Alternatively or additionally, techniques are used that are described in U.S. Provisional Patent Application 60/426,182, filed Nov. 14, 2002, entitled, "Stimulation circuitry and control of electronic medical device," which is assigned to the assignee of the present application and is incorporated herein by reference.

Typically, once electrode support 58 is properly placed, endoscopic device 30 (see FIG. 2) is removed from the patient, and receiver 78 or receiver 100 remains in the patient, typically immediately above or below the hard palate or at the ridge of the eye, and is connected by leads to the electrodes on electrode support 58. Note that keyhole opening 42 in hollow sleeve 36 and slit 43 in handle 38 allow for the removal of these items without affecting leads 74, because the leads pass through the keyhole and slit as the handle and sleeve are removed. Alternatively, sleeve 36 is made so as to split along its length prior to removal.

Figure 10:
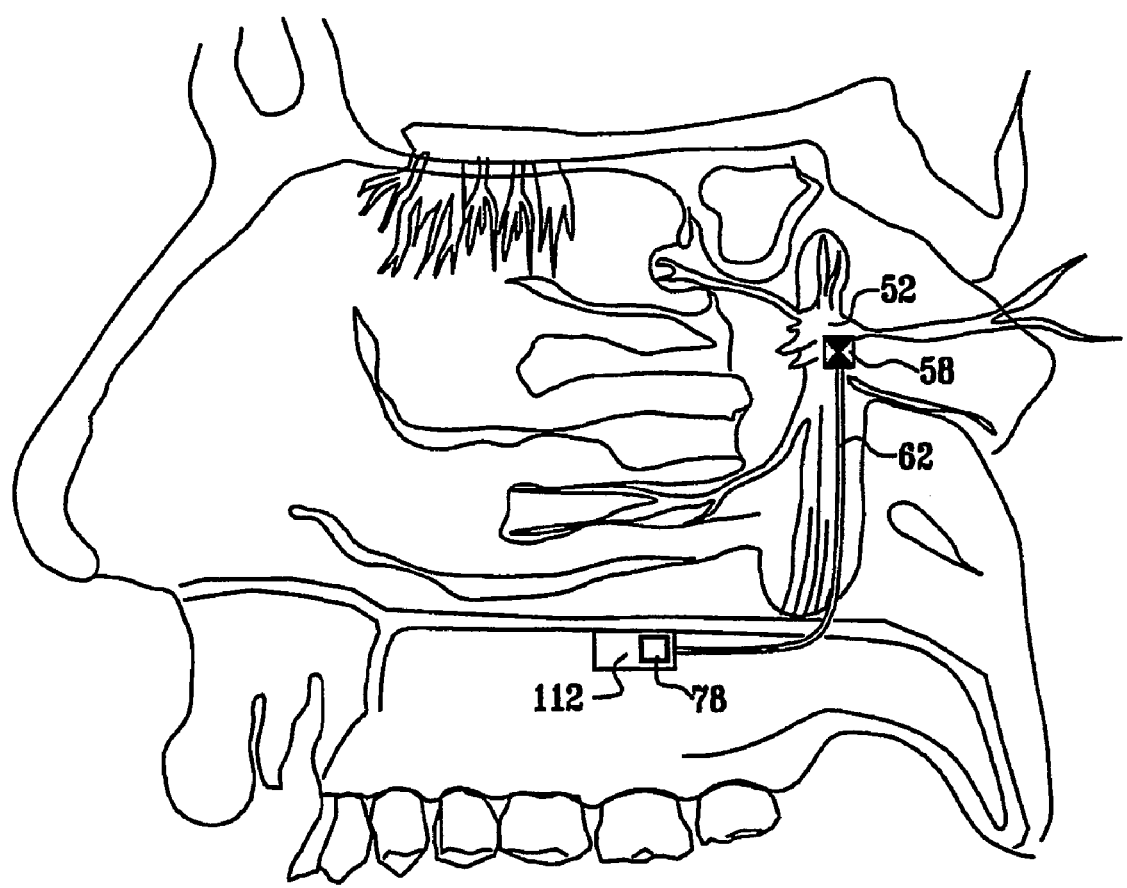
FIG. 10 is a schematic, sectional illustration of the placement of an electrode in the SPG system and a control unit on the upper jaw, in accordance with an embodiment of the present invention.

FIG. 10 shows the placement of electrode support 58 adjacent to SPG 52 and the placement of a stimulator 112 comprising receiver 78 in the supraperiosteal region of the hard palate of the patient, typically at midline, in accordance with an embodiment of the present invention. Alternatively, stimulator 112 is implanted in the nasal cavity on the upper surface of the hard palate. Typically, stimulator 112 receives power wirelessly from an external control unit temporarily placed in or near the mouth. Stimulator 112 is typically fixed to the hard palate with microscrews. Alternatively, the control unit powers and controls stimulator 112 by a wired connection between the control unit and a receiver 100 (FIG. 9B) incorporated into the stimulator. Further alternatively, one or more lead wires are brought out through the skin and coupled to an external control unit.

Typically, but not necessarily, techniques described in PCT Patent Publication WO 01/85094 to Shalev and Gross, entitled, "Method and apparatus for stimulating the sphenopalatine ganglion to modify properties of the BBB and cerebral blood flow," or the US national phase application thereof, U.S. patent application Ser. No. 10/258,714, filed Oct. 25, 2002, both of which are assigned to the assignee of the present patent application and incorporated herein by reference, are adapted for use with the techniques of these embodiments of the present invention. In particular, electrodes implanted adjacent to the SPG, using the relatively minimally-invasive surgical techniques and associated surgical tools of the present invention, are driven by a stimulator (e.g. control unit), using control and driving circuitry and treatment protocols described therein, to control the blood brain barrier and/or treat neurological symptoms or disease.

In an embodiment of the present invention, a combined trans-maxillary sinus and trans-nasal endoscopic-assisted approach to the SPG is used in order to implant at least one electrode in a region of the SPG. Typically, to start the procedure, the patient is given a local and topical anesthesia in the intraoral vestibulum at the area of the canine fossa, and a topical intranasal anesthesia at the region of the lateral nasal wall of the operated side. The posterior wall of the maxillary sinus is typically dissected, and the anterior part of the sphenopalatine fossa is dissected via a trans-maxillary approach. Typically, the dissection is performed approximately 0.5 mm from the medial wall of the maxillary sinus under direct endoscopic visualization.

Typically, a complete nasal endoscopic examination is performed on both sides and then under direct visualization an incision is made about 0.4-about 0.8 mm under the second conchae on the operating side. A mucoperiosteal flap is typically raised posteriorly and inferiorly followed by dissection and clamping of the sphenopalatine artery. Subsequently, under direct visualization, the lateral wall of the nose is typically penetrated and the sphenopalatine fossa is approached. In an embodiment of the present invention, the surgeon now approaches the SPG via the trans-maxillary sinus. In another embodiment, the surgeon approaches the SPG via the trans-nasal approach. The specific approach is typically dependent on the anatomical topography of the patient.

At this stage of the procedure, endoscopic device 30 (see FIG. 2) is typically inserted in the dissected tissue and used to place an electrode adjacent to the SPG, as discussed hereinabove for the endoscopic transpalatine approach to the SPG.

Yet another embodiment of the present invention comprises an upper blepharoplasty approach to the anterior and/or posterior ethmoidal nerves, in order to implant at least one electrode adjacent to the anterior and/or posterior ethmoidal nerves. Typically, to start the procedure, the patient's upper and lower eyelids are sterilized. A local anesthetic is typically applied to the upper eyelid. Once the anesthetic has taken effect, an incision in the skin following an eyelid crest is typically performed. In an embodiment, the incision is approximately 15 mm long.

Once the skin has been dissected, the orbicularis muscle is typically passed through by performing a blunt dissection. Subsequently, a sharp incision of the periosteum, typically about 15 mm in length, is made on the superomedial aspect of the orbit. Typically, the subperiosteal tissue is then dissected to expose the anterior ethmoidal foramen and its contents, including the anterior ethmoidal nerve. Alternatively or additionally, the dissection is performed so as to expose the posterior ethmoidal nerve. Once the anterior and/or posterior ethmoidal nerve has been exposed, at least one electrode is implanted adjacent to the nerve.

Figure 11:
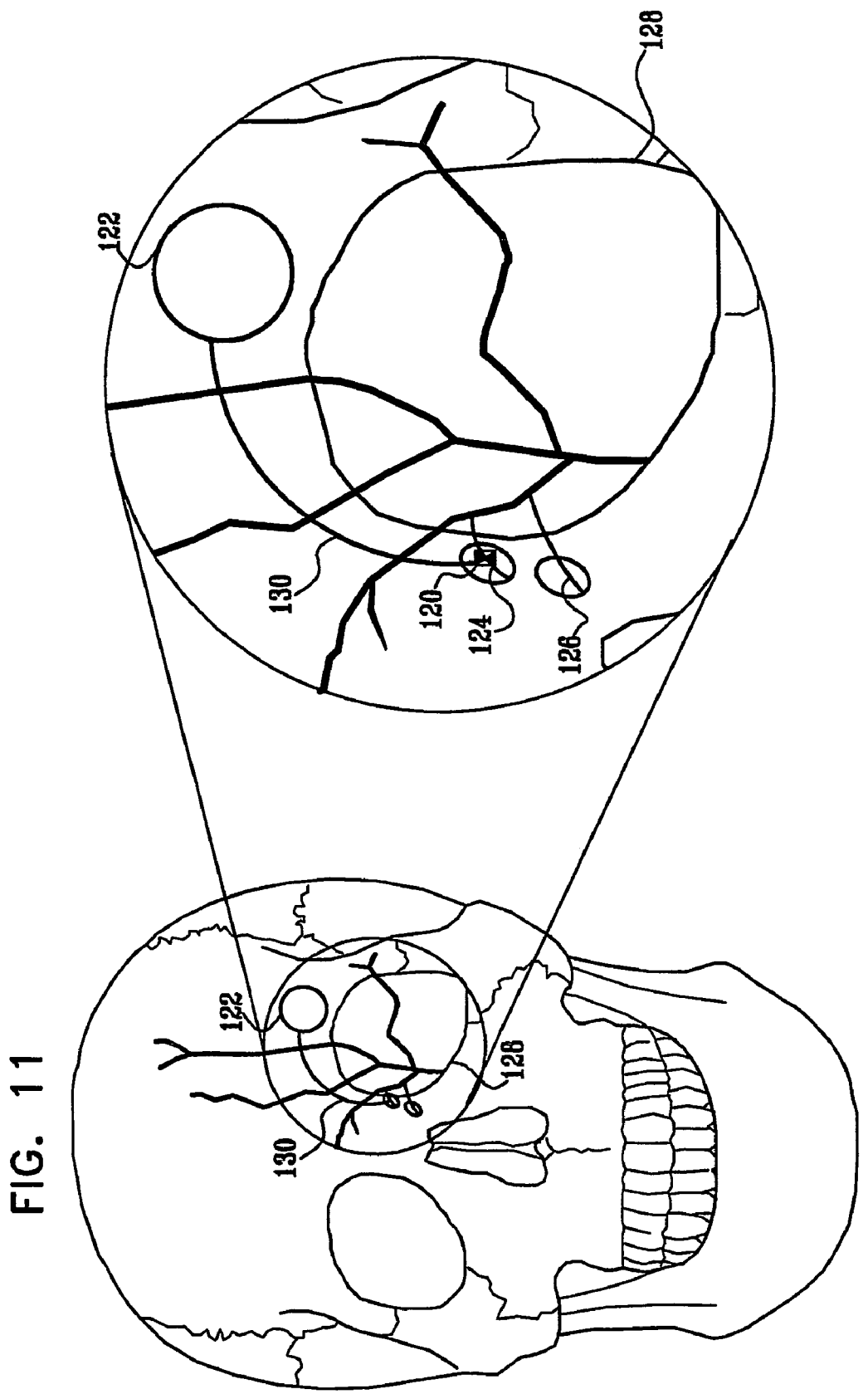
FIG. 11 is a schematic, pictorial illustration of the placement of an electrode adjacent to the anterior ethmoidal nerve and a control unit on the orbital rim, in accordance with an embodiment of the present invention.

FIG. 11 shows the placement of an electrode 120 adjacent to the posterior ethmoidal nerve 124 in the region of an orbital cavity 128, in accordance with an embodiment of the present invention. Typically, electrode 120 is coupled to a stimulator 122 by a lead 130. Stimulator 122 is typically fixed to the superior orbital rim. Following placement of electrode 120, lead 130, and stimulator 122, incisions in the periosteum, muscle and skin are closed with standard surgical techniques.

Alternatively, electrode 120 is placed adjacent to an anterior ethmoidal nerve 126. Further alternatively, a plurality of electrodes 120 is placed so as to stimulate both the anterior and the posterior ethmoidal nerves.

Typically, verification and/or optimization of the electrode nerve interface after the electrodes are placed is performed by observing the effects of stimulation on one or more physiological responses. Potential observations include, but are not limited to: (1) evaluating the vasodilatation of blood vessels of the eye, (2) assessment of cerebral blood flow by using trans-cranial Doppler, (3) assessment of forehead perfusion by using Laser-Doppler, and (4) assessment of forehead perfusion by a temperature sensor.

Figure 12:
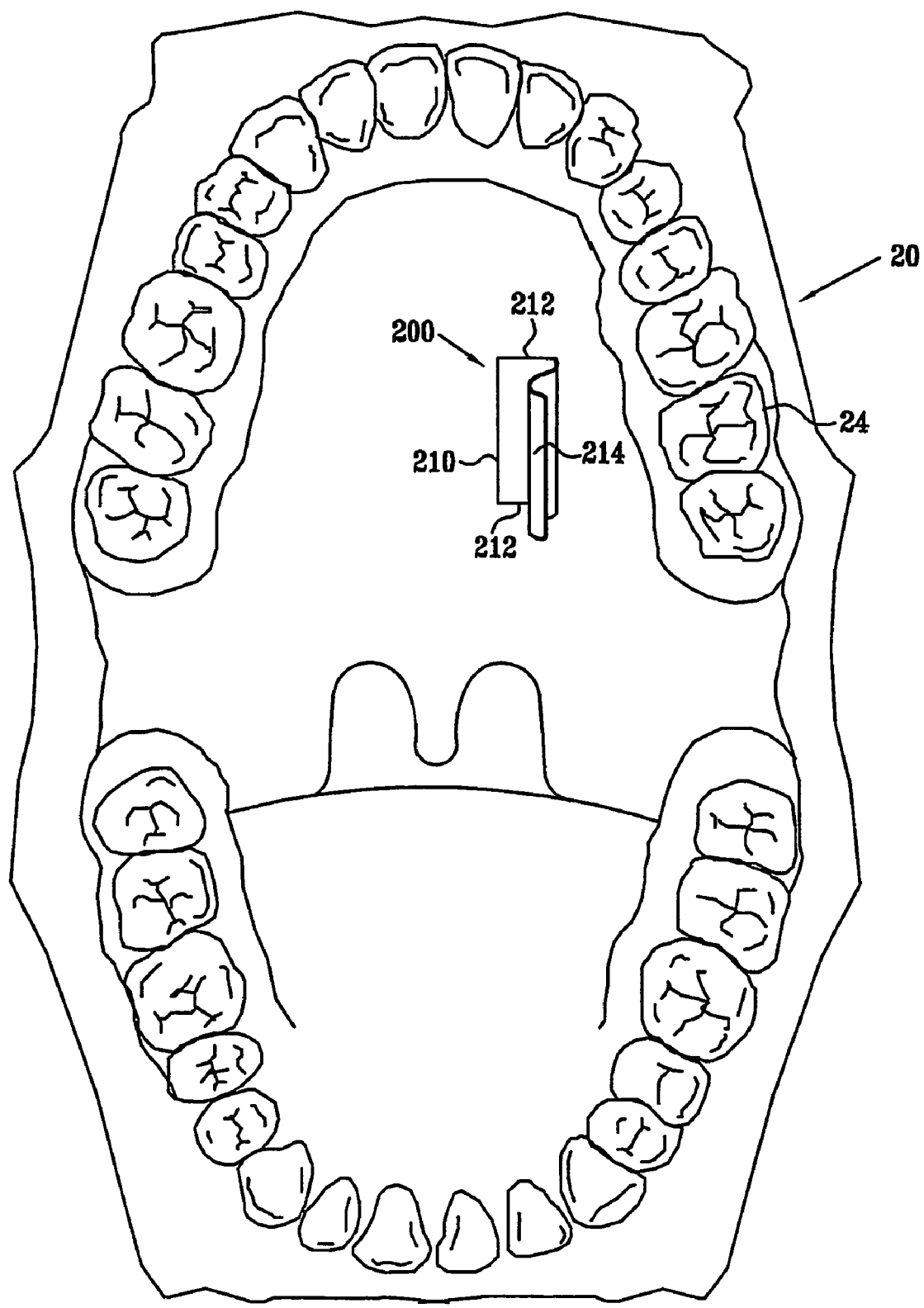
FIG. 12 is a schematic, pictorial illustration showing incisions in a roof of an oral cavity and associated anatomical structures, in accordance with an embodiment of the present invention.

FIG. 12 is a schematic, pictorial illustration showing incisions 200 in a roof of oral cavity 20 and associated anatomical structures, where dissection commences in a surgical procedure to access the SPG system, in accordance with an embodiment of the present invention. In this embodiment, soft tissue is dissected to expose greater palatine foramen 22 (see FIG. 1), in order to allow access via the greater palatine canal to the SPG system by means of a transpalatine approach.

Prior to beginning the surgical procedure, the patient is typically instructed to rinse his mouth with an antimicrobial oral rinse, such as 0.2% chlorhexidine solution, for at least about five minutes. For some patients, the surgical procedure is performed under general anesthesia To begin the procedure, the patient is typically positioned with an open mouth (typically using a mouth gag). Greater palatine foramen 22 (FIG. 1) is then located, typically by the anatomical landmark of second upper molar 24. (Greater palatine foramen 22 is typically located 1 cm medial to second upper molar 24 at the border between the hard and the soft palates.) The area of greater palatine foramen 22 is anesthetized, such as by 2 ml lidocaine. A full-thickness about 3 cm mucogingival incision 210 is made at the midline of the hard palate, including about 0.5 cm of the soft palate. Two releasing incisions 212, about 1 cm each, are made at the ends of midline incision 210. Typically, electrosurgery is used to make these releasing incisions in order to minimize bleeding. A mucoperiosteal flap 214 is raised, and the greater palatine neurovascular bundle is carefully exposed, typically using Jeter cleft palate scissors and a periosteal elevator, such as an Obwegeser periosteal elevator. The neuromuscular bundle is typically preserved using a molt curette. Mucoperiosteal flap 214 is gently and firmly retracted using a flap retractor, such as a Jensen flap retractor, revealing the contents of greater palatine foramen 22.

Figure 13:
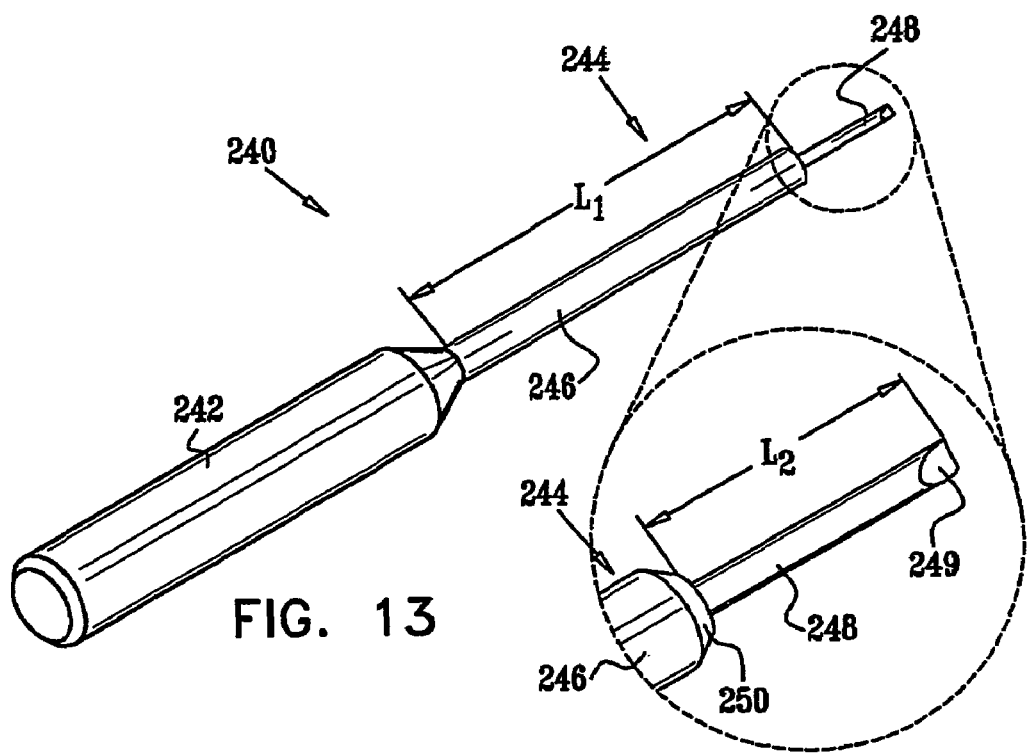
FIG. 13 is a schematic illustration of a stylet, in accordance with an embodiment of the present invention.

FIG. 13 is a schematic illustration of a stylet 240, which is the first instrument to be inserted into the greater palatine canal once the contents of greater palatine foramen 22 have been dissected and revealed, in accordance with an embodiment of the present invention. Stylet 240 comprises a handle 242 and a rod 244 coupled to the handle, such as with a screw (screw not shown). Rod 244 comprises a proximal rod shaft 246 and a narrower distal rod shaft 248. Proximal rod shaft 246 typically has a length $L_1$ of between about 20 mm and about 150 mm, such as about 88 mm or about 100 mm, and a diameter of between about 1.5 mm and about 6 mm, such as about 4 mm or about 4.6 mm. Distal rod shaft 248 typically has a length $L_2$ of between about 3 mm and about 20 mm, such as about 10 mm or about 12 mm, and a diameter of between about 1 mm and about 1.5 mm, such as about 1.3 mm. A distal tip of distal rod shaft 248 typically comprises a cutting implement 249, such as a blade. Typically, rod 244 is shaped so as to define a shoulder 250 between proximal rod shaft 246 and distal rod shaft 248. Shoulder 250 is adapted to prevent insertion of distal rod shaft 248 into the sphenopalatine fossa beyond the depth of the greater palatine canal.

Figure 14:
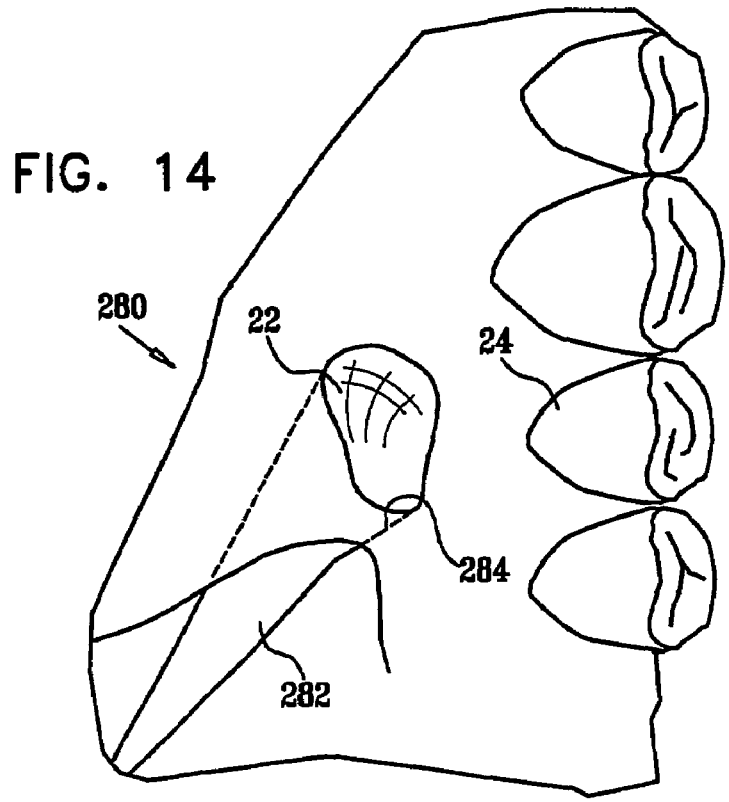
FIG. 14 is a schematic, pictorial illustration of a posterolateral roof of an oral cavity, in accordance with an embodiment of the present invention.

FIG. 14 is a schematic, pictorial illustration of a posterolateral roof 280 of oral cavity 20 (FIG. 1), in accordance with an embodiment of the present invention. Shown in the figure are greater palatine foramen 22, a greater palatine canal 282, and a posterior wall 284 of greater palatine canal 282. During the surgical procedure, stylet 240 is inserted posteriorly through the greater palatine canal to the greater palatine neurovascular bundle, and supported against posterior wall 284. Stylet 240 is pushed vertically using a gentle plus and minus 45-degree clockwise and counterclockwise rotational motion, until shoulder 250 of stylet 240 (FIG. 13) reaches the exposed entrance to greater palatine foramen 22 (at the roof of the mouth).

FIGS. 15A and 15B are schematic illustrations of a passive tip periosteal elevator 300 used to widen the path created using stylet 240, in accordance with embodiments of the present invention. Passive tip periosteal elevator 300 comprises a handle 310 and a rod 312 coupled to the handle, such as with a screw (screw not shown). Rod 312 comprises a proximal rod shaft 314 and a distal rod shaft 316, a distal tip 318 of which is typically rounded. Proximal rod shaft 314 typically has a length $L_3$ of between about 30 mm and about 150 mm, such as about 70 mm or about 100 mm, and a diameter of between about 2 mm and about 6 mm, such as about 4 mm or about 4.6 mm. Distal rod shaft 316 typically has a length $L_4$ of between about 15 mm and about 50 mm, such as about 30 mm or about 40 mm, and a diameter of between about 1 mm and about 2 mm. Typically, passive tip periosteal elevators having certain distal rod shaft 248 diameters (such as between about 1 mm and about 1.4 mm) have a rounded distal rod shaft (configuration not shown in figures), while passive tip periosteal elevators having other distal rod shaft 248 diameters (such as greater than about 1.4 mm) have a distal rod shaft with at least one flattened surface 320, as shown in the figures. Optionally, flattened surface 320 is shaped to define file-like slots 322, having a depth of about 0.2 mm, for example.

For some applications, distal rod shaft 316 is straight, as shown in FIG. 15A, while for other applications, distal rod shaft 316 is bent, as shown in FIG. 15B. Such a bend is typically located between about 3 mm and about 10 mm, such as about 4 mm, from distal tip 318, and typically has an angle between about 5 degrees and about 15 degrees, such as about 10 degrees.

During the surgical procedure, after stylet 240 has been removed, a series of passive tip periosteal elevators 300, having successively greater distal rod shaft 316 diameters, is typically used to widen the path created using stylet 240. First, the narrowest passive tip periosteal elevator of the series (e.g., having a distal rod shaft 316 diameter of about 1 mm) is introduced through the path created by stylet 240, keeping tight contact between the instrument and posterior wall 284 of greater palatine canal 282. This insertion is typically performed with a plus and minus 45-degree clockwise and counterclockwise rotational motion and gentle abrading maneuver. If using a passive tip periosteal elevator having a flattened surface, as described hereinabove, the flattened surface is typically used for the abrading maneuver. The passive tip periosteal elevator is typically inserted into the greater palatine canal to a depth of about 25 mm. Alternatively, the depth of the greater palatine canal is measured prior to or during the implantation procedure, in which case the tip is inserted to the measured depth. Typically, the depth of insertion is indicated on the elevator by one or more marks 324 on distal rod shaft 316.

The first, narrowest, passive tip periosteal elevator is removed, and this widening step of the surgical procedure is repeated using elevators having successively wider distal rod shaft diameters, until greater palatine canal 282 is widened, typically, to about 2 mm. Generally, irrigation and suction are performed between periosteal elevator replacements in order to remove osseous debris.

Figure 16:
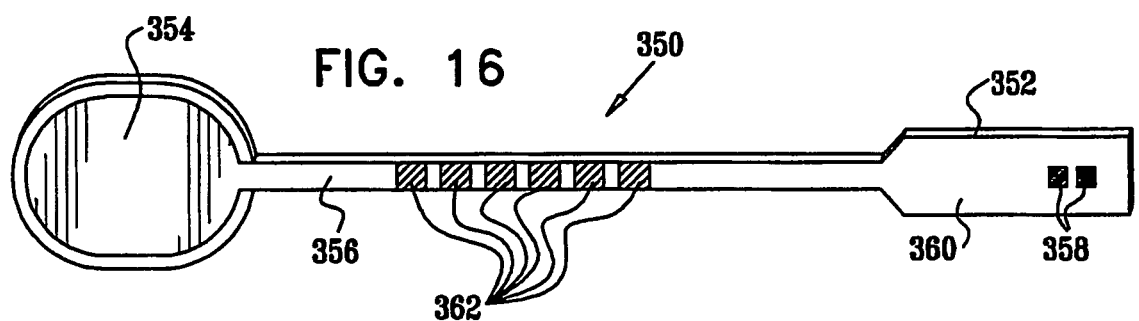
FIG. 16 is a schematic illustration of an implantable neural stimulator, in accordance with an embodiment of the present invention.

FIG. 16 is a schematic illustration of an implantable neural stimulator 350, in accordance with an embodiment of the present invention. Stimulator 350 comprises an electrode support 352, a receiver 354, and a connecting element 356, such as a connecting tube. (Other suitable structures for connecting element 356 will be apparent to one of ordinary skill in the art, having read the disclosure of the present patent application.) Electrode support 352 comprises one or more electrodes 358, positioned on an electrode surface 360 of the support, such that the electrodes are in contact with a target site (e.g., the SPG) when stimulator 350 is implanted. For some applications, electrodes 358 are arranged in the electrode configuration described hereinbelow with reference to FIG. 17. Alternatively, for other applications, electrodes 358 are arranged in one of the electrode configurations described hereinabove with reference to FIGS. 5A, 5B, or 5C. Receiver 354 receives power and control signals from a control unit that drives electrodes 358. For some applications, receiver 354 is similar to receiver 78 or receiver 100, described hereinabove with reference to FIG. 9A and FIG. 9B, respectively. Alternatively, other suitable configurations are utilized. Optionally, connecting element 356 comprises one or more marks 362 that indicate the depth of insertion of stimulator 350 into the greater palatine canal.

Figure 17:
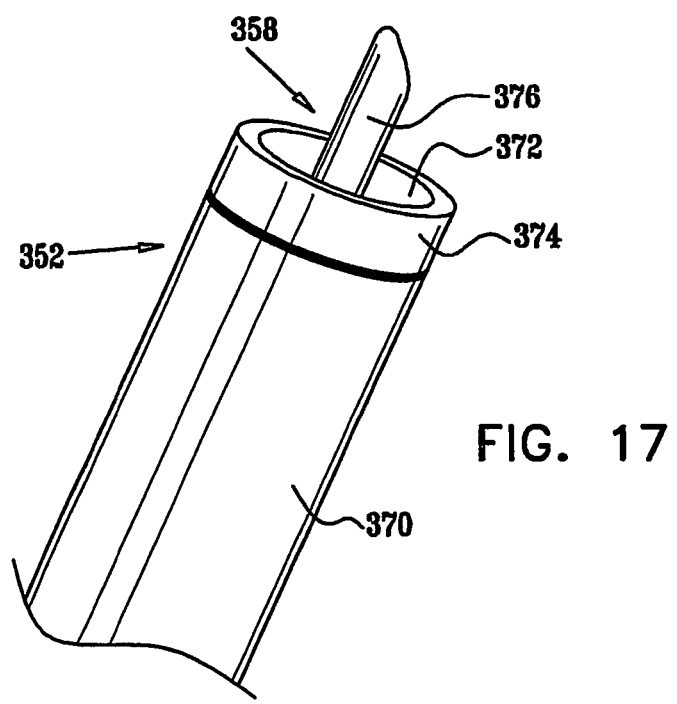
FIG. 17 shows an electrode configuration for use with an electrode support of the stimulator of FIG. 16, in accordance with an embodiment of the present invention.

FIG. 17 shows an electrode configuration for use with electrode support 352, in accordance with an embodiment of the present invention. In this configuration, electrode support 352 comprises two insulated regions: an insulated shaft region 370 and an insulated tip region 372. Electrodes 358 comprise an annular electrode 374 and a rod electrode 376, electrically isolated from one another by insulated tip region 372.

Figure 18:
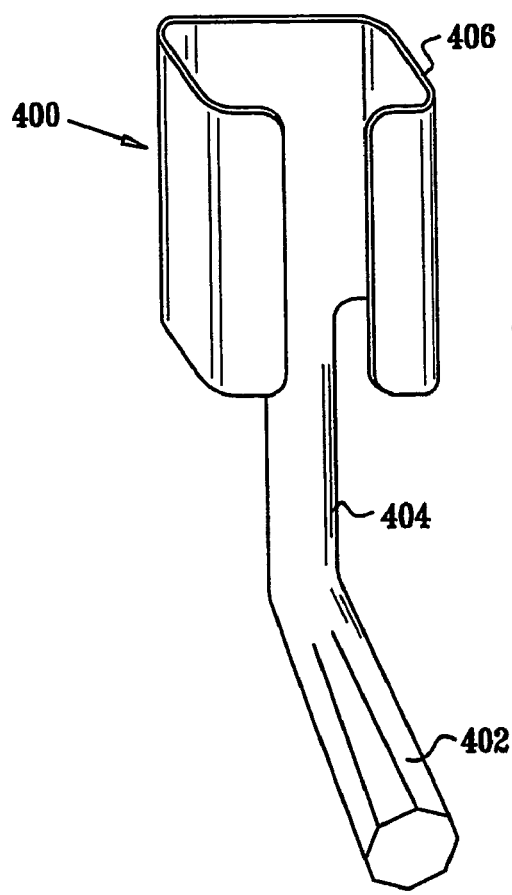
FIG. 18 is a schematic illustration of an electrode introducer, in accordance with an embodiment of the present invention.

FIG. 18 is a schematic illustration of an electrode introducer 400, in accordance with an embodiment of the present invention. Introducer 400 is used for introducing stimulator 350 into the greater palatine canal. Introducer 400 typically comprises a handle 402 for manipulating the introducer, a rod 404, to which electrode support 352 (FIG. 16) is attached, and a protective sleeve 406.

Figure 19:
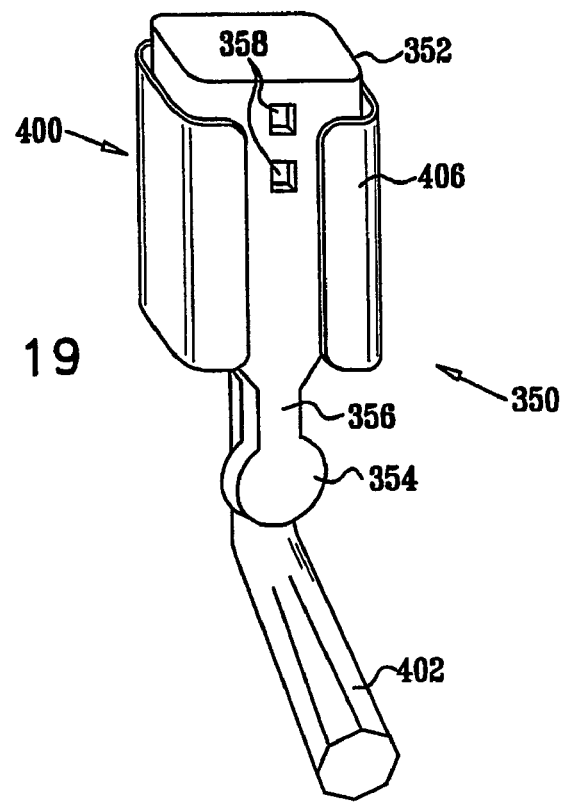
FIG. 19 is a schematic illustration of the stimulator of FIG. 16 mounted on the electrode introducer of FIG. 18, in accordance with an embodiment of the present invention.

FIG. 19 is a schematic illustration (not necessarily to scale) of stimulator 350 mounted on electrode introducer 400, in accordance with an embodiment of the present invention. Stimulator 350 is mounted on electrode introducer 400 by inserting electrode support 352 into protective sleeve 406.

During the surgical procedure, after greater palatine canal 282 has been widened, electrode introducer 400 is inserted into greater palatine canal 282, typically to depth of about 25 mm. Alternatively, the depth of the greater palatine canal is measured prior to or during the implantation procedure, in which case the introducer is inserted to the measured depth. If connecting element 356 comprises marks 362, as described hereinabove with reference to FIG. 16, such marks are typically used to determine the depth of the introducer. Typically, electrode surface 360 of stimulator 350 is placed in contact with the posterior aspect of the SPG. Mucoperiosteal flap 214 (FIG. 12) is sutured over receiver 354, which is located flush with the palatine bone, typically using forceps, such as Adson forceps, and a needle holder.

Figure 20:
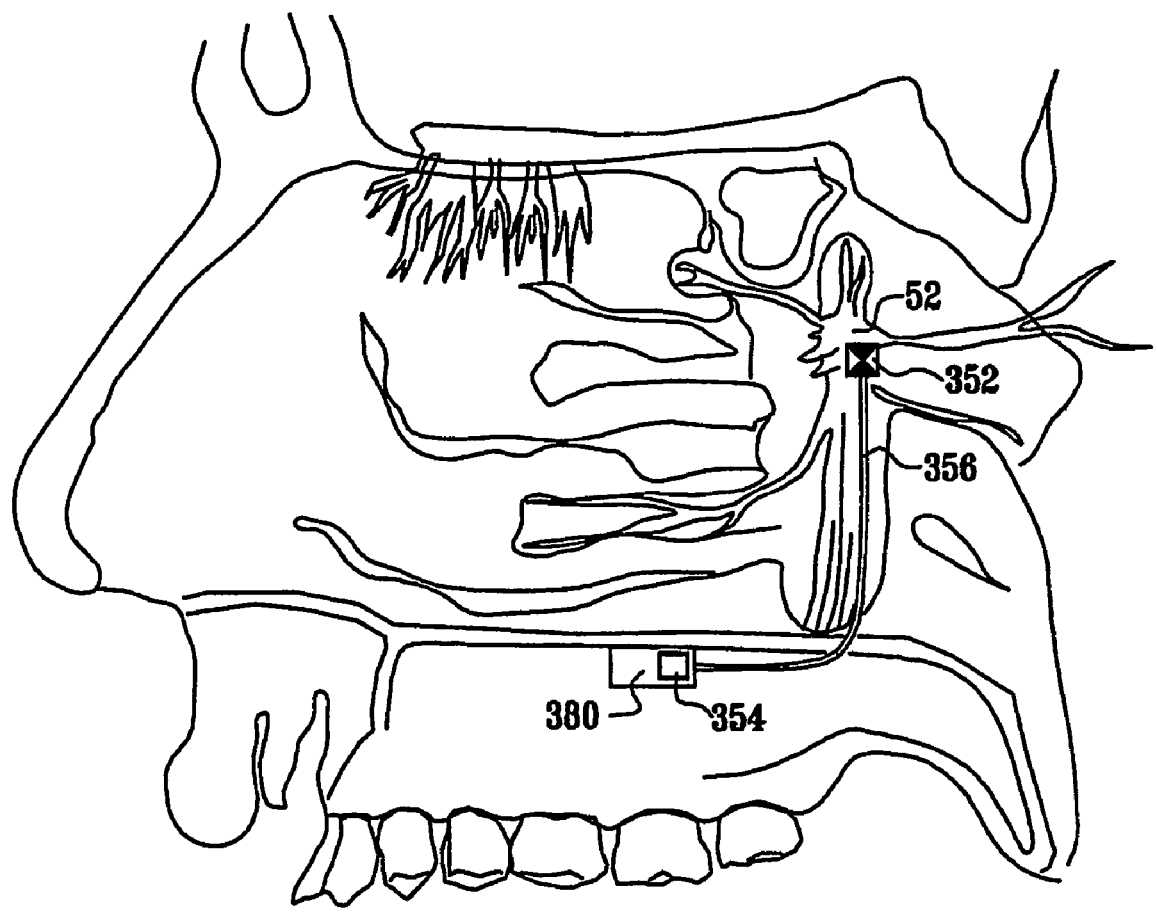
FIG. 20 is a schematic, sectional illustration of the placement of an electrode in the SPG system and a control unit on the upper jaw, in accordance with an embodiment of the present invention.

FIG. 20 shows the placement of electrode support 352 posteriorly adjacent to SPG 52 and the placement of a stimulator 380 comprising receiver 354 in the supraperiosteal region of the hard palate of the patient, typically at midline, in accordance with an embodiment of the present invention. Alternatively, stimulator 112 is implanted in the nasal cavity on the upper surface of the hard palate. Typically, stimulator 380 receives power wirelessly from an external control unit temporarily placed in or near the mouth. Stimulator 380 is typically fixed to the hard palate with microscrews. Further alternatively, one or more lead wires are brought out through the skin and coupled to an external control unit. Still further alternatively, stimulator 380 is battery powered, and comprises control circuitry to allow it to operate independently of outside control.

In some embodiments, techniques described herein are practiced in combination with techniques described in one or both of the following co-assigned US applications: (i) U.S. patent application Ser. No. 10/294,310, filed Nov. 14, 2002, and a corresponding PCT application claiming priority therefrom, filed on even date herewith, entitled, "Stimulation for treating eye pathologies," and (ii) U.S. Provisional Patent Application 60/426,182, filed Nov. 14, 2002, entitled, "Stimulation circuitry and control of electronic medical device." All of these applications are incorporated herein by reference.

Techniques described in this application may be practiced in combination with methods and apparatus described in one or more of the following patent applications, which are assigned to the assignee of the present patent application and are incorporated herein by reference:

U.S. patent application Ser. No. 10/258,714, filed Oct. 25, 2002, entitled, "Method and apparatus for stimulating the sphenopalatine ganglion to modify properties of the BBB and cerebral blood flow," or the above-referenced PCT Publication WO 01/85094

U.S. Provisional Patent Application 60/364,451, filed Mar. 15, 2002, entitled, "Applications of stimulating the sphenopalatine ganglion (SPG)"

U.S. Provisional Patent Application 60/368,657, filed Mar. 28, 2002, entitled, "SPG Stimulation"

U.S. Provisional Patent Application 60/376,048, filed Apr. 25, 2002, entitled, "Methods and apparatus for modifying properties of the BBB and cerebral circulation by using the neuroexcitatory and/or neuroinhibitory effects of odorants on nerves in the head"

U.S. Provisional Patent Application 60/388,931, filed Jun. 14, 2002, entitled "Methods and systems for management of Alzheimer's disease"

U.S. Provisional Patent Application 60/400,167, filed Jul. 31, 2002, entitled, "Delivering compounds to the brain by modifying properties of the BBB and cerebral circulation"

U.S. Provisional Patent Application 60/426,180, filed Nov. 14, 2002, entitled, "Surgical tools and techniques for sphenopalatine ganglion stimulation"

U.S. Provisional Patent Application 60/426,182, filed Nov. 14, 2002, entitled, "Stimulation circuitry and control of electronic medical device"

U.S. patent application Ser. No. 10/294,310, filed Nov. 14, 2002, entitled, "SPG stimulation for treating eye pathologies"

U.S. patent application Ser. No. 10/294,343, filed Nov. 14, 2002, and a corresponding PCT application claiming priority therefrom, filed on even date herewith, entitled, "Administration of anti-inflammatory drugs into the CNS"

U.S. Provisional Patent Application 60/426,181, filed Nov. 14, 2002, entitled, "Stimulation for treating ear pathologies"

U.S. Provisional Patent Application 60/448,807, filed Feb. 20, 2003, entitled, "Stimulation for treating autoimmune-related disorders of the CNS"

U.S. Provisional Patent Application 60/461,232 to Gross et al., filed Apr. 8, 2003, entitled, "Treating abnormal conditions of the mind and body by modifying properties of the blood-brain barrier and cephalic blood flow"

a PCT Patent Application to Shalev, filed Apr. 25, 2003, entitled, "Methods and apparatus for modifying properties of the BBB and cerebral circulation by using the neuroexcitatory and/or neuroinhibitory effects of odorants on nerves in the head"

a U.S. provisional patent application, filed Sep. 26, 2003, entitled, "Diagnostic applications of stimulation"

a U.S. patent application, filed Oct. 2, 2003, entitled, "Targeted release of nitric oxide in the brain circulation for opening the BBB"

a PCT patent application, filed on even date herewith,. entitled, "Stimulation circuitry and control of electronic medical device"

a PCT patent application, filed on even date herewith, entitled, "Stimulation for treating ear pathologies"

It is noted that the figures depicting embodiments of the present invention are not necessarily drawn to scale, and, instead, may change certain dimensions in order to more clearly demonstrate some aspects of the invention.

It will be appreciated by persons skilled in the art that the present invention is not limited to what has been particularly shown and described hereinabove. Rather, the scope of the present invention includes both combinations and subcombinations of the various features described hereinabove, as well as variations and modifications thereof that are not in the prior art, which would occur to persons skilled in the art upon reading the foregoing description.

The invention claimed is:

1. A method comprising:
widening at least a portion of a greater palatine canal of a subject;
passing a treatment stimulation device through a greater palatine foramen of the subject;
bringing the device into contact with a vicinity of a site of the subject, the site selected from the group consisting of: a sphenopalatine ganglion (SPG) of the subject and a neural tract originating in or leading to the SPG;
applying stimulation with the device; and
configuring the stimulation to be sufficient to induce a change in cerebral blood flow of the subject.

2. The method according to claim 1, wherein the site includes the SPG of the subject, and wherein bringing the device into contact with the vicinity of the site comprises bringing the device into contact with the vicinity of the SPG.

3. The method according to claim 1, wherein the site includes a vidian nerve of the subject, and wherein bringing the device into contact with the vicinity of the site comprises bringing the device into contact with the vicinity of the vidian nerve.

4. The method according to claim 1, wherein the site includes an ethmoidal nerve of the subject, and wherein bringing the device into contact with the vicinity of the site comprises bringing the device into contact with the vicinity of the ethmoidal nerve.

5. The method according to claim 1, wherein the site includes a retro-orbital branch of the SPG of the subject, and wherein bringing the device into contact with the vicinity of the site comprises bringing the device into contact with the retro-orbital branch.

6. The method according to claim 1, wherein bringing the device into contact comprises:
observing one or more physiological responses of the subject to the stimulation; and
verifying desired placement of the device responsive to the observation.

7. The method according to claim 1, wherein the stimulation device includes at least one electrode, and wherein bringing the device into contact comprises bringing the electrode into contact with the vicinity of the site.

8. The method according to claim 7, wherein bringing the electrode into contact comprises wrapping the electrode around a nerve of the subject in the vicinity of the site.

9. The method according to claim 1, wherein the stimulation device includes a stimulator, the method comprising fixing the stimulator to a hard palate of the subject.

10. The method according to claim 9, wherein fixing the stimulator to the hard palate comprises coupling the stimulator to a supraperiosteal region of the hard palate.

11. The method according to claim 9, wherein fixing the stimulator to the hard palate comprises coupling the stimulator to an upper surface of the hard palate in a nasal cavity of the subject.

12. The method according to claim 9, wherein fixing the stimulator to the hard palate comprises coupling the stimulator to a lower surface of the hard palate.

13. The method according to claim 1, wherein passing the device through the greater palatine foramen comprises determining a depth of insertion of the device in a greater palatine canal of the subject by observing at least one mark on the device indicative of the depth of the insertion.

14. The method according to claim 1, wherein widening the greater palatine canal of the subject comprises using a series of tools having successively greater diameters.

15. The method according to claim 1, wherein passing the device through the greater palatine foramen comprises mounting the device on an introducer, and passing the introducer through the greater palatine foramen.

16. The method according to claim 1, wherein bringing the device into contact comprises implanting the device in the vicinity of the site.

17. The method according to claim 1, wherein widening the greater palatine canal comprises using a series of periosteal elevators having successively greater diameters.

18. The method according to claim 1, wherein widening the greater palatine canal comprises abrading.

19. The method according to claim 1, wherein widening the greater palatine canal comprises removing osseous debris.

20. A method comprising:
widening at least a portion of a greater palatine canal of a subject;
passing a treatment stimulation device through the at least a portion of the greater palatine canal;
bringing the device into contact with a vicinity of a site of the subject, the site selected from the group consisting of: a sphenopalatine ganglion (SPG) of the subject and a neural tract originating in or leading to the SPG; and
applying stimulation with the device; and
configuring the stimulation to be sufficient to induce a change in cerebral blood flow of the subject.

21. The method according to claim 20, wherein passing the device through the portion of the greater palatine canal comprises determining a depth of insertion of the device in the greater palatine canal by observing at least one mark on the device indicative of the depth of the insertion.

22. The method according to claim 20, wherein passing the device through the at least a portion of the greater palatine canal comprises passing the device through at least about 2 cm of the greater palatine canal.

23. The method according to claim 20, wherein widening the portion comprises using a series of tools having successively greater diameters.

24. The method according to claim 20, wherein passing the device through the at least a portion of the greater palatine canal comprises mounting the device on an introducer, and passing the introducer through the portion.

25. The method according to claim 20, wherein bringing the device into contact comprises implanting the device in the vicinity of the site.

26. The method according to claim 20, wherein the site includes the SPG of the subject, and wherein bringing the device into contact with the vicinity of the site comprises bringing the device into contact with the vicinity of the SPG.

27. The method according to claim 20, wherein the site includes a vidian nerve of the subject, and wherein bringing the device into contact with the vicinity of the site comprises bringing the device into contact with the vicinity of the vidian nerve.

28. The method according to claim 20, wherein the site includes an ethmoidal nerve of the subject, and wherein bringing the device into contact with the vicinity of the site comprises bringing the device into contact with the vicinity of the ethmoidal nerve.

29. The method according to claim 20, wherein the site includes a retro-orbital branch of the SPG of the subject, and wherein bringing the device into contact with the vicinity of the site comprises bringing the device into contact with the retro-orbital branch.

30. The method according to claim 20, wherein bringing the device into contact comprises:
   observing one or more physiological responses of the subject to the stimulation; and
   verifying desired placement of the device responsive to the observation.

31. The method according to claim 20, wherein the stimulation device includes at least one electrode, and wherein bringing the device into contact comprises bringing the electrode into contact with the vicinity of the site.

32. The method according to claim 31, wherein bringing the electrode into contact comprises wrapping the electrode around a nerve of the subject in the vicinity of the site.

33. The method according to claim 20, wherein the stimulation device includes a stimulator, the method comprising fixing the stimulator to a hard palate of the subject.

34. The method according to claim 33, wherein fixing the stimulator to the hard palate comprises coupling the stimulator to a supraperiosteal region of the hard palate.

35. The method according to claim 33, wherein fixing the stimulator to the hard palate comprises coupling the stimulator to an upper surface of the hard palate in a nasal cavity of the subject.

36. The method according to claim 33, wherein fixing the stimulator to the hard palate comprises coupling the stimulator to a lower surface of the hard palate.

37. The method according to claim 20, wherein widening the portion comprises using a series of periosteal elevators having successively greater diameters.

38. The method according to claim 20, wherein widening the portion comprises abrading.

39. The method according to claim 20, wherein widening the portion comprises removing osseous debris.

40. A method comprising:
   passing a treatment stimulation device through a greater palatine foramen of a subject;
   bringing the device into contact with a vicinity of a site of the subject, the site selected from the group consisting of: a sphenopalatine ganglion (SPG) of the subject and a neural tract originating in or leading to the SPG;
   applying stimulation with the device; and
   configuring the stimulation to be sufficient to modulate permeability of a blood-brain-barrier of the subject.

41. The method according to claim 40, wherein the site includes the SPG of the subject, and wherein bringing the device into contact with the vicinity of the site comprises bringing the device into contact with the vicinity of the SPG.

42. The method according to claim 40, wherein the site includes a vidian nerve of the subject, and wherein bringing the device into contact with the vicinity of the site comprises bringing the device into contact with the vicinity of the vidian nerve.

43. The method according to claim 40, wherein the site includes an ethmoidal nerve of the subject, and wherein bringing the device into contact with the vicinity of the site comprises bringing the device into contact with the vicinity of the ethmoidal nerve.

44. The method according to claim 40, wherein the site includes a retro-orbital branch of the SPG of the subject, and wherein bringing the device into contact with the vicinity of the site comprises bringing the device into contact with the retro-orbital branch.

45. The method according to claim 40, wherein bringing the device into contact comprises:
   observing one or more physiological responses of the subject to the stimulation; and
   verifying desired placement of the device responsive to the observation.

46. The method according to claim 40, wherein the stimulation device includes a stimulator, the method comprising fixing the stimulator to a hard palate of the subject.

47. The method according to claim 46, wherein fixing the stimulator to the hard palate comprises coupling the stimulator to a supraperiosteal region of the hard palate.

48. The method according to claim 46, wherein fixing the stimulator to the hard palate comprises coupling the stimulator to an upper surface of the hard palate in a nasal cavity of the subject.

49. The method according to claim 46, wherein fixing the stimulator to the hard palate comprises coupling the stimulator to a lower surface of the hard palate.

50. The method according to claim 40, wherein bringing the device into contact comprises implanting the device in the vicinity of the site.

51. The method according to claim 40, wherein passing the device through the greater palatine foramen comprises widening a greater palatine canal of the subject.

52. The method according to claim 51, wherein widening the greater palatine canal comprises abrading.

53. The method according to claim 51, wherein widening the greater palatine canal comprises removing osseous debris.

54. A method comprising:
   passing a treatment stimulation device through at least a portion of a greater palatine canal of a subject;
   bringing the device into contact with a vicinity of a site of the subject, the site selected from the group consisting of: a sphenopalatine ganglion (SPG) of the subject and a neural tract originating in or leading to the SPG;
   applying stimulation with the device; and
   configuring the stimulation to be sufficient to modulate permeability of a blood-brain-barrier of the subject.

55. The method according to claim 54, wherein bringing the device into contact comprises implanting the device in the vicinity of the site.

56. The method according to claim 54, wherein the site includes the SPG of the subject, and wherein bringing the device into contact with the vicinity of the site comprises bringing the device into contact with the vicinity of the SPG.

57. The method according to claim 54, wherein the site includes a vidian nerve of the subject, and wherein bringing the device into contact with the vicinity of the site comprises bringing the device into contact with the vicinity of the vidian nerve.

58. The method according to claim 54, wherein the site includes an ethmoidal nerve of the subject, and wherein bringing the device into contact with the vicinity of the site comprises bringing the device into contact with the vicinity of the ethmoidal nerve.

59. The method according to claim 54, wherein the site includes a retro-orbital branch of the SPG of the subject, and wherein bringing the device into contact with the vicinity of the site comprises bringing the device into contact with the retro-orbital branch.

60. The method according to claim 54, wherein bringing the device into contact comprises:

observing one or more physiological responses of the subject to the stimulation; and verifying desired placement of the device responsive to the observation.

61. The method according to claim 54, wherein the stimulation device includes a stimulator, the method comprising fixing the stimulator to a hard palate of the subject.

62. The method according to claim 61, wherein fixing the stimulator to the hard palate comprises coupling the stimulator to a supraperiosteal region of the hard palate.

63. The method according to claim 61, wherein fixing the stimulator to the hard palate comprises coupling the stimulator to an upper surface of the hard palate in a nasal cavity of the subject.

64. The method according to claim 61, wherein fixing the stimulator to the hard palate comprises coupling the stimulator to a lower surface of the hard palate.

65. The method according to claim 54, wherein passing the device through the at least a portion of the greater palatine canal comprises widening the portion.

66. The method according to claim 65, wherein widening the portion palatine canal comprises abrading.

67. The method according to claim 65, wherein widening the portion comprises removing osseous debris.

* * * * *